US007572889B2

(12) United States Patent
Flannagan et al.

(10) Patent No.: US 7,572,889 B2
(45) Date of Patent: Aug. 11, 2009

(54) *BT* TOXIN RECEPTORS FROM LEPIDOPTERAN INSECTS

(75) Inventors: Ronald D. Flannagan, Grimes, IA (US); Terry EuClaire Meyer, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 282 days.

(21) Appl. No.: 11/192,967

(22) Filed: Jul. 29, 2005

(65) Prior Publication Data

US 2005/0262587 A1    Nov. 24, 2005

Related U.S. Application Data

(62) Division of application No. 09/715,909, filed on Nov. 17, 2000, now Pat. No. 7,060,491.

(60) Provisional application No. 60/234,099, filed on Sep. 21, 2000, provisional application No. 60/166,285, filed on Nov. 18, 1999.

(51) Int. Cl.
C07K 14/705    (2006.01)
(52) U.S. Cl. .................................. 530/350; 530/402
(58) Field of Classification Search .................. None
See application file for complete search history.

(56) References Cited

U.S. PATENT DOCUMENTS

| 5,693,491 | A  | 12/1997 | Bulla et al. |
| 5,804,393 | A  | 9/1998  | Geiser et al. |
| 6,007,981 | A  | 12/1999 | Bulla |
| 6,423,502 | B2 | 7/2002  | Bulla et al. |
| 6,660,497 | B1 | 12/2003 | Bulla et al. |

FOREIGN PATENT DOCUMENTS

| WO | WO 96/12964    | 5/1996  |
| WO | WO 98/59048    | 12/1998 |
| WO | WO 01/34807 A2 | 5/2001  |

OTHER PUBLICATIONS

Dorsch, J., "Isolation and Characterization of the Insecticidal Toxin Binding Site From the Receptor BT-$R_1$ of *Manduca Sexta*," A Dissertation submitted to the Department of Molecular Biology and the Graduate School of the University of Wyoming, 1998.
Estruch, J. et al., "Transgenic Plants: An Emerging Approach to Pest Control," *Nature Biotechnology*, 1997, vol. 15, pp. 137-141.
Francis, B., et al., "Further Characterization of BT-$R_1$, The Cadherin-Like Receptor for Cry 1AB Toxin in Tobacco Hornworm (*Manduca sexta*) Midguts, Insect," *Biochem. Mol. Biol.*, 1997, vol. 27(6), pp. 541-550.
Franklin, S., et al., "Southern Analysis of BT-$R_1$, The *Manduca Sexta* Gene Encoding The Receptor for the CrylAB Toxin of *Bacillus Thuringiensis*," *Mol. Gen. Genet*, 1997, vol. 256, pp. 517-524.

Gahan, L.J., et al., "Identification of a Gene Associated with Bt Resistance in Heliothis Virescens," *Science* (2001) pp. 857-860, vol. 293.
Garczynski, S., et al., "Identification of Putative Insect Brush Border Membrane-Binding Molecules Specific to *Bacillus Thuringiensis* δ-Endotoxin by Protein Blot Analysis, Applied Environmental Microbiology," 1991, vol. 57(10), pp. 2816-2820.
Gill, S, et al., "Identification, Isolation, and Cloning of a *Bacillus Thuringiensis* CrylAc Toxin-Binding Protein from the Midgut of the Lepidopteran Insect Heliothis Virescens," *The Journal of Biological Chemistry*, 1995, vol. 270(45), pp. 27277-27282.
Hofte, et al., "Insecticidal Crystal Proteins of *Bacillus Thuringiensis*," *Microbiological Reviews*, 1989, vol. 53(2), pp. 242-255.
Hua, G., et al., "Binding Analyses of *Bacillus Thuringiensis* Cry δ-Endotoxins Using Brush Border Membrane Vesicles of *Ostrinia Nubilalis*," *Applied and Environmental Microbiology*, 2001, vol. 67(2), pp. 872-879.
Ihara, H., et al., "Purification and Partial Amino Acid Sequences of the Binding Protein from Bombyx Mori for CrylAa δ-endotoxin of *Bacillus Thuringiensis*," *Elsevier Science Inc.*, 1998, pp. 197-204.
Keeton, T., et al., "Effects of Midgut-Protein-Preparative and Ligand Binding Procedures on the Toxin Binding Characteristics of BT-$R_1$, A Common High-Affinity Receptor in Manduca Sexta for Cryl A *Bacillus Thuringiensis* Toxins," *Applied and Environmental Microbiology*, 1998, vol. 64(6), pp. 2158-2165.
Keeton, T., et al., "Ligand Specificity and Affinity of BT-$R_1$, The *Bacillus Thuringiensis* Cryl A Toxin Receptor From *Manduca Sexta*, Expressed in Mammalian and Insect Cell Cultures," *Applied and Environmental Microbiology*, 1997, vol. 63(9), pp. 3419-3425.
Knight, P., et al., "The Receptor for *Bacillus Thuringiensis* CrylA(c) Delta-Endotoxin in the Brush Border Membrane of the Lepidopteran *Manduca Sexta* is Aminopeptidase N," *Molecular Microbiology*, 1994, vol. 11(3), pp. 429-436.
Lee, M., et al., "Aminopeptidase N Purified from Gypsy Moth Brush Border Membrane Vesicles Is a Specific Receptor for *Bacillus Thuringiensis* CrylAc Toxin," *Applied and Environmental Microbiology*, 1996, vol. 62(8), pp. 2845-2849.
McGaughey, W., et al., "RT Resistance Management A Plan for Reconciling the Needs of the Many Stakeholders in Bt-Based Products," *Nature Biotechnology*, 1998, vol. 16, pp. 144-146.
Matty, W.S.A., "Identification, Purification and Cloning of a High-Affinity Invertebrate Protocadherin Receptor BT-$R_2$ From the Pink Bollworm (*Pectinophora gossypiella*) for *Bacillus Thuringiensis* CRY1A Toxins," Jul. 1999, Dissertation submitted to the Dept. of Molecular Biology and The Graduate School of the University of Wyoming.
Midboe, E.G., "Characterization of the BT-$R_1$ Gene and Its Expression in *Manduca Sexta*," Jul. 1999, Dissertation submitted to the Dept. of Molecular Biology and The Graduate School of the University of Wyoming.

(Continued)

*Primary Examiner*—Robert C Hayes
(74) *Attorney, Agent, or Firm*—Alston & Bird LLP

(57) ABSTRACT

The invention relates to Bt toxin resistance management. The invention particularly relates to the isolation and characterization of nucleic acid and polypeptides for a novel Bt toxin receptor. The nucleic acid and polypeptides are useful in identifying and designing novel Bt toxin receptor ligands including novel insecticidal toxins.

3 Claims, 1 Drawing Sheet

OTHER PUBLICATIONS

Nagamatsu, Y., et al., "Cloning, Sequencing, and Expression of the Bombyx Mori Receptor for *Bacillus Thurigiensis* Insecticidal CrylA(A) Toxin," *Biosci. Biotechnol. Biochem*, 1998, vol. 62(4), pp. 727-734.

Nagamatsu, Y. et al., "The Cadherin-Like Protein is Essential to Specificity Determination and Cytotoxic Action of the *Bacillus Thuringiensis* Insecticidal CrylAa Toxin," *Febs Letters*, 1999, vol. 460, pp. 385-390.

Oddou, P., et al., "Immunologically Unrelated Heliothis Sp. And Spodoptera Sp. Midgut Membrane-Proteins Bind *Bacillus Thuringiensis* CrylA(b) δ-endotoxin," *Eur. J. Biochem.*, 1993, vol. 212, pp. 145-150.

Roush, R., et al., "Assessing the Odds: The Emergence of Resistance to BT Transgenic Plants," *Nature Biotechnology*, 1997, vol. 15, pp. 816-817.

Skolnick, J. et al., "From Genes to Protein Structure and Function: Novel Applications of Computational Approaches in the Genomic Era," *Trends in Biotechnology*, pp. 34-39, vol. 18, No. 1.

Vadlamudi, R., et al., "Cloning and Expression of a Receptor for an Insecticidal Toxin of *Bacillus Thuringiensis*," *The Journal of Biological Chemistry*, 1995, vol. 270(10), pp. 5490-5494.

Vadlamudi, R., et al., "A Specific Binding Protein from *Manduca Sexta* for the Insecticidal Toxin of *Bacillus Thuringiensis* Subsp. Berliner," *The Journal of Biological Chemistry*, 1993, vol. 268(17), pp. 12334-12340.

Rudinger, J., "Characteristics of the Amino Acids as Components of a Peptide Hormone Sequence," *J.A. Parsons University*, 1976, Park Press, Baltimore, pp. 1-7.

Gly = putative glycosilation sites

Cad = cadherin-like domain

FIGURE 1

SEQUENCE LISTING

<160> NUMBER OF SEQ ID NOS: 11

<210> SEQ ID NO 1
<211> LENGTH: 5498
<212> TYPE: DNA
<213> ORGANISM: Ostrinia nubilalis
<220> FEATURE:
<221> NAME/KEY: CDS
<222> LOCATION: (162)...(5312)

<400> SEQUENCE: 1

```
cataataaca ataagagga agtgtgtgtg aaaaacgaag aagttaataa acctggataa          60
ttaaacctga aaaaaccgg tgtttaagtg gaatttttgc tgaaggacaa ccgtgggata         120
gctcaaatat taaaattcta cataactaag gatcatgcaa a atg ggg gtt gag agg       176
                                              Met Gly Val Glu Arg
                                                1               5 ttc ttc cca gca gtg cta ctg gtc tct tta gcc tct gcc gca cta gcc         224
Phe Phe Pro Ala Val Leu Leu Val Ser Leu Ala Ser Ala Ala Leu Ala
             10                  15                  20 aac caa cga tgt tcg tac att atc gca ata cca aga ccg gag act ccg         272
Asn Gln Arg Cys Ser Tyr Ile Ile Ala Ile Pro Arg Pro Glu Thr Pro
         25                  30                  35 gaa ctg ccg cct att gat tac gaa gga aaa tca tgg agt gaa cag cct         320
Glu Leu Pro Pro Ile Asp Tyr Glu Gly Lys Ser Trp Ser Glu Gln Pro
     40                  45                  50 cta ata ccc ggc ccg acc cga gag gaa gta tgt atg gag aac ttc tta         368
Leu Ile Pro Gly Pro Thr Arg Glu Glu Val Cys Met Glu Asn Phe Leu
 55                  60                  65 ccg gat caa atg att cag gtc ata tac atg gag gaa gaa atc gaa gga         416
Pro Asp Gln Met Ile Gln Val Ile Tyr Met Glu Glu Glu Ile Glu Gly
 70                  75                  80                  85 gac gtc atc att gcg aag ctt aac tat caa ggg tcc aac acg ccg gtg         464
Asp Val Ile Ile Ala Lys Leu Asn Tyr Gln Gly Ser Asn Thr Pro Val
                 90                  95                 100 ctg tcg att atg tca ggc cag ccc aga gcc cag ctg ggc cct gag ttt         512
Leu Ser Ile Met Ser Gly Gln Pro Arg Ala Gln Leu Gly Pro Glu Phe
             105                 110                 115 cga cag aat gaa gca gac ggc caa tgg agc ctt gtt att acg caa aga         560
Arg Gln Asn Glu Ala Asp Gly Gln Trp Ser Leu Val Ile Thr Gln Arg
         120                 125                 130 caa gac tac gag aca gca acc atg cag agc tat gtg ttc tca atc caa         608
Gln Asp Tyr Glu Thr Ala Thr Met Gln Ser Tyr Val Phe Ser Ile Gln
    135                 140                 145 gtg gag ggt gaa tca cag gcc gta ctg gtg gcg ctg gag ata gtc aac         656
Val Glu Gly Glu Ser Gln Ala Val Leu Val Ala Leu Glu Ile Val Asn
150                 155                 160                 165 atc gac gac aat ccg ccc atc ctg caa gtg gtc agc gcc tgc gta att         704
Ile Asp Asp Asn Pro Pro Ile Leu Gln Val Val Ser Ala Cys Val Ile
                170                 175                 180 cca gaa cat ggc gag gct aga ctg acc gac tgc gtg tac caa gtg tca         752
Pro Glu His Gly Glu Ala Arg Leu Thr Asp Cys Val Tyr Gln Val Ser
            185                 190                 195 gac cgc gac ggt gaa atc agc acc cgc ttc atg acg ttc cgt gtc gac         800
Asp Arg Asp Gly Glu Ile Ser Thr Arg Phe Met Thr Phe Arg Val Asp
        200                 205                 210 agc agc agg gct gca gat gaa agc atc ttc tac atg gtt gga gaa tac         848
Ser Ser Arg Ala Ala Asp Glu Ser Ile Phe Tyr Met Val Gly Glu Tyr
    215                 220                 225
```

```
gac ccc agc gac tgg ttc aat atg aag atg act gtg ggg atc aat tcg      896
Asp Pro Ser Asp Trp Phe Asn Met Lys Met Thr Val Gly Ile Asn Ser
230                 235                 240                 245 ccc ttg aac ttc gag aca act cag ctt cat ata ttt agc gtc aca gct      944
Pro Leu Asn Phe Glu Thr Thr Gln Leu His Ile Phe Ser Val Thr Ala
                250                 255                 260 tct gac tcg cta ccg aac aac cac acg gtc acc atg atg gtg caa gtg      992
Ser Asp Ser Leu Pro Asn Asn His Thr Val Thr Met Met Val Gln Val
            265                 270                 275 gag aac gta gag tct cgg ccc cct cgc tgg gtg gag atc ttc tca gtg     1040
Glu Asn Val Glu Ser Arg Pro Pro Arg Trp Val Glu Ile Phe Ser Val
        280                 285                 290 cag cag ttt gac gag aag act aat cag agc ttc tcc ctc cgc gcg ata     1088
Gln Gln Phe Asp Glu Lys Thr Asn Gln Ser Phe Ser Leu Arg Ala Ile
    295                 300                 305 gac ggg gac acg gga atc aat agg gcc atc aac tat acc ctc atc agg     1136
Asp Gly Asp Thr Gly Ile Asn Arg Ala Ile Asn Tyr Thr Leu Ile Arg
310                 315                 320                 325 gat gac gct gac gac ttc ttt tcc ctg gag gtg att gaa gac gga gct     1184
Asp Asp Ala Asp Asp Phe Phe Ser Leu Glu Val Ile Glu Asp Gly Ala
                330                 335                 340 att ctg cac gtg act gag atc gac cgc gac aag ctt gaa aga gag ctt     1232
Ile Leu His Val Thr Glu Ile Asp Arg Asp Lys Leu Glu Arg Glu Leu
            345                 350                 355 ttc aac ctc acc atc gtt gct tac aaa tct act gac gct agc ttt gca     1280
Phe Asn Leu Thr Ile Val Ala Tyr Lys Ser Thr Asp Ala Ser Phe Ala
        360                 365                 370 aca gag gcc cac att ttc atc atc gtc aac gac gtc aat gat cag cga     1328
Thr Glu Ala His Ile Phe Ile Ile Val Asn Asp Val Asn Asp Gln Arg
    375                 380                 385 ccc gag ccg ctg cat aaa gaa tac agt att gat atc atg gag gaa act     1376
Pro Glu Pro Leu His Lys Glu Tyr Ser Ile Asp Ile Met Glu Glu Thr
390                 395                 400                 405 cca atg act cta aac ttc aat gaa gaa ttt gga ttc cat gat cga gat     1424
Pro Met Thr Leu Asn Phe Asn Glu Glu Phe Gly Phe His Asp Arg Asp
                410                 415                 420 ttg ggt gaa aac gct caa tac aca gtg gaa ctt gag gac gtg ttc ccg     1472
Leu Gly Glu Asn Ala Gln Tyr Thr Val Glu Leu Glu Asp Val Phe Pro
            425                 430                 435 cca ggg gcg gcg tcc gca ttc tac atc gcg ccg ggg agc ggc tac cag     1520
Pro Gly Ala Ala Ser Ala Phe Tyr Ile Ala Pro Gly Ser Gly Tyr Gln
        440                 445                 450 agg cag acc ttc atc atg ggc acc ata aac cac acc atg ctg gat tac     1568
Arg Gln Thr Phe Ile Met Gly Thr Ile Asn His Thr Met Leu Asp Tyr
    455                 460                 465 gaa gat gtc att ttt cag aac atc atc att aag gtc aaa gca gtg gac     1616
Glu Asp Val Ile Phe Gln Asn Ile Ile Ile Lys Val Lys Ala Val Asp
470                 475                 480                 485 atg aac aac gct agc cac gtg ggc gag gcg ctg gtg tac gtg aac ctg     1664
Met Asn Asn Ala Ser His Val Gly Glu Ala Leu Val Tyr Val Asn Leu
                490                 495                 500 atc aac tgg aac gac gaa ctt ccc atc ttc gag gag agc agc tac tcc     1712
Ile Asn Trp Asn Asp Glu Leu Pro Ile Phe Glu Glu Ser Ser Tyr Ser
            505                 510                 515 gcg tcg ttt aag gag acc gtc ggc gcc ggc ttc ccg gtg gcc acg gtg     1760
Ala Ser Phe Lys Glu Thr Val Gly Ala Gly Phe Pro Val Ala Thr Val
        520                 525                 530 ctc gcc ctc gac aga gac atc gac gac gta gta gtg cat tca ttg atg     1808
Leu Ala Leu Asp Arg Asp Ile Asp Asp Val Val Val His Ser Leu Met
    535                 540                 545
```

| | | |
|---|---|---|
| ggc aac gct gtt gac tac ctg ttc ata gat gaa tca acg gga gag atc<br>Gly Asn Ala Val Asp Tyr Leu Phe Ile Asp Glu Ser Thr Gly Glu Ile<br>550                    555                    560                    565 | 1856 |
| ttc gtg agc atg gac gat gcc ttc gac tac cac cga cag aac act cta<br>Phe Val Ser Met Asp Asp Ala Phe Asp Tyr His Arg Gln Asn Thr Leu<br>                    570                    575                    580 | 1904 |
| ttt gtt cag gtg cgc gct gac gat act ttg ggc gac ggc cca cac aac<br>Phe Val Gln Val Arg Ala Asp Asp Thr Leu Gly Asp Gly Pro His Asn<br>          585                    590                    595 | 1952 |
| aca gtg acc acc cag ctg gtg ata gaa ctg gag gat gtc aac aac act<br>Thr Val Thr Thr Gln Leu Val Ile Glu Leu Glu Asp Val Asn Asn Thr<br>600                    605                    610 | 2000 |
| cct ccc acc cta cgc ttg ccc cgt tcg act cca agc gtc gag gag aac<br>Pro Pro Thr Leu Arg Leu Pro Arg Ser Thr Pro Ser Val Glu Glu Asn<br>          615                    620                    625 | 2048 |
| gtt ccc gaa gga tac gag ata tcc cgg gaa atc act gct acc gac ccg<br>Val Pro Glu Gly Tyr Glu Ile Ser Arg Glu Ile Thr Ala Thr Asp Pro<br>630                    635                    640                    645 | 2096 |
| gac acc agc gcc tac ctg tgg ttc gag atc gac tgg gac tcc acc tgg<br>Asp Thr Ser Ala Tyr Leu Trp Phe Glu Ile Asp Trp Asp Ser Thr Trp<br>                    650                    655                    660 | 2144 |
| gcc acc aag cag ggc aga gag acc aac cct act gaa tac gtc ggg tgt<br>Ala Thr Lys Gln Gly Arg Glu Thr Asn Pro Thr Glu Tyr Val Gly Cys<br>          665                    670                    675 | 2192 |
| ata gtt atc gaa acg ata tac ccc acc gag ggc aac cgg ggt tcc gcc<br>Ile Val Ile Glu Thr Ile Tyr Pro Thr Glu Gly Asn Arg Gly Ser Ala<br>680                    685                    690 | 2240 |
| atc ggg cgc ctc gtg gtg caa gag atc cgg gac aac gtc acc atc gac<br>Ile Gly Arg Leu Val Val Gln Glu Ile Arg Asp Asn Val Thr Ile Asp<br>          695                    700                    705 | 2288 |
| ttc gag gaa ttc gag atg ctt tac ctc acc gtc cgc gtg agg gac ctc<br>Phe Glu Glu Phe Glu Met Leu Tyr Leu Thr Val Arg Val Arg Asp Leu<br>710                    715                    720                    725 | 2336 |
| aac act gtc atc gga gat gac tac gat gag gcg acg ttc acg atc aca<br>Asn Thr Val Ile Gly Asp Asp Tyr Asp Glu Ala Thr Phe Thr Ile Thr<br>                    730                    735                    740 | 2384 |
| ata atc gac atg aac gac aac gcg ccg atc ttc gcg aac ggc acg ctg<br>Ile Ile Asp Met Asn Asp Asn Ala Pro Ile Phe Ala Asn Gly Thr Leu<br>          745                    750                    755 | 2432 |
| acg cag acg atg cgc gtg cgc gag ctg gcg gcc agc ggc acg ctc atc<br>Thr Gln Thr Met Arg Val Arg Glu Leu Ala Ala Ser Gly Thr Leu Ile<br>                    760                    765                    770 | 2480 |
| ggc tcc gtg ctc gcc acc gac atc gac ggc ccg ctc tac aac caa gtg<br>Gly Ser Val Leu Ala Thr Asp Ile Asp Gly Pro Leu Tyr Asn Gln Val<br>775                    780                    785 | 2528 |
| cgc tac act ata caa cct aga aac aac act ccc gag gga tta gtg aag<br>Arg Tyr Thr Ile Gln Pro Arg Asn Asn Thr Pro Glu Gly Leu Val Lys<br>790                    795                    800                    805 | 2576 |
| att gac ttc aca act ggt caa att gag gtg gat gcg aac gag gcg atc<br>Ile Asp Phe Thr Thr Gly Gln Ile Glu Val Asp Ala Asn Glu Ala Ile<br>                    810                    815                    820 | 2624 |
| gat gca gac gaa ccc tgg cgc ttc tac ttg tac tac acc gtc atc gct<br>Asp Ala Asp Glu Pro Trp Arg Phe Tyr Leu Tyr Tyr Thr Val Ile Ala<br>          825                    830                    835 | 2672 |
| agc gac gag tgc tcc ctg gaa aac cgc acg gaa tgt cct cca gat tcc<br>Ser Asp Glu Cys Ser Leu Glu Asn Arg Thr Glu Cys Pro Pro Asp Ser<br>          840                    845                    850 | 2720 |
| aac tac ttc gaa gtt cca ggc gat atc gaa ata gaa atc atc gac aca<br>Asn Tyr Phe Glu Val Pro Gly Asp Ile Glu Ile Glu Ile Ile Asp Thr | 2768 |

-continued

|  |  |  |  |  |  |  |  |  |  |  |  |  |  |  |  |
|---|---|---|---|---|---|---|---|---|---|---|---|---|---|---|---|
| | 855 | | | | | 860 | | | | | 865 | | | | |

| aac | aac | aaa | gtg | cct | gag | ccg | ctc | act | gag | aag | ttc | aac | acg | acg | gtg | 2816 |
|---|---|---|---|---|---|---|---|---|---|---|---|---|---|---|---|---|
| Asn | Asn | Lys | Val | Pro | Glu | Pro | Leu | Thr | Glu | Lys | Phe | Asn | Thr | Thr | Val | |
| 870 | | | | | 875 | | | | | 880 | | | | | 885 | |

| tac | gtc | tgg | gag | aat | gcc | acg | agc | ggc | gac | gag | gtg | gtc | cag | ctg | tac | 2864 |
|---|---|---|---|---|---|---|---|---|---|---|---|---|---|---|---|---|
| Tyr | Val | Trp | Glu | Asn | Ala | Thr | Ser | Gly | Asp | Glu | Val | Val | Gln | Leu | Tyr | |
| | | | | 890 | | | | | 895 | | | | | 900 | | |

| tcc | cac | gac | cgt | gac | aga | gac | gag | ttg | tac | cac | acg | gta | cga | tac | acg | 2912 |
|---|---|---|---|---|---|---|---|---|---|---|---|---|---|---|---|---|
| Ser | His | Asp | Arg | Asp | Arg | Asp | Glu | Leu | Tyr | His | Thr | Val | Arg | Tyr | Thr | |
| | | | 905 | | | | | 910 | | | | | 915 | | | |

| atg | aac | ttt | gcg | gtg | aac | ccc | cga | ctg | cgg | gat | ttc | ttc | gag | gtg | gac | 2960 |
|---|---|---|---|---|---|---|---|---|---|---|---|---|---|---|---|---|
| Met | Asn | Phe | Ala | Val | Asn | Pro | Arg | Leu | Arg | Asp | Phe | Phe | Glu | Val | Asp | |
| | | | 920 | | | | | 925 | | | | | 930 | | | |

| ctg | gac | act | ggt | cgc | ctt | gag | gtg | cat | tac | ccg | ggg | gac | gaa | aaa | ttg | 3008 |
|---|---|---|---|---|---|---|---|---|---|---|---|---|---|---|---|---|
| Leu | Asp | Thr | Gly | Arg | Leu | Glu | Val | His | Tyr | Pro | Gly | Asp | Glu | Lys | Leu | |
| | | | 935 | | | | | 940 | | | | | 945 | | | |

| gac | cgc | gat | ggg | gat | gag | cct | aca | cat | act | atc | ttt | gta | aat | ttc | atc | 3056 |
|---|---|---|---|---|---|---|---|---|---|---|---|---|---|---|---|---|
| Asp | Arg | Asp | Gly | Asp | Glu | Pro | Thr | His | Thr | Ile | Phe | Val | Asn | Phe | Ile | |
| 950 | | | | | 955 | | | | | 960 | | | | | 965 | |

| gat | aac | ttc | ttt | tct | gat | ggt | gac | ggt | agg | aga | aac | cag | gac | gaa | gtt | 3104 |
|---|---|---|---|---|---|---|---|---|---|---|---|---|---|---|---|---|
| Asp | Asn | Phe | Phe | Ser | Asp | Gly | Asp | Gly | Arg | Arg | Asn | Gln | Asp | Glu | Val | |
| | | | | 970 | | | | | 975 | | | | | 980 | | |

| gaa | ata | ttt | gtc | gtt | cta | ttg | gat | gtg | aac | gac | aac | gct | cct | gag | atg | 3152 |
|---|---|---|---|---|---|---|---|---|---|---|---|---|---|---|---|---|
| Glu | Ile | Phe | Val | Val | Leu | Leu | Asp | Val | Asn | Asp | Asn | Ala | Pro | Glu | Met | |
| | | | | 985 | | | | | 990 | | | | | 995 | | |

| cca | ttg | cct | gat | gaa | ctc | cgg | ttt | gat | gtt | tcc | gaa | gga | gca | gtt | gct | 3200 |
|---|---|---|---|---|---|---|---|---|---|---|---|---|---|---|---|---|
| Pro | Leu | Pro | Asp | Glu | Leu | Arg | Phe | Asp | Val | Ser | Glu | Gly | Ala | Val | Ala | |
| | | | | 1000 | | | | | 1005 | | | | | 1010 | | |

| ggt | gtc | cgt | gta | ctc | cca | gaa | atc | tac | gca | ccg | gac | agg | gat | gaa | cca | 3248 |
|---|---|---|---|---|---|---|---|---|---|---|---|---|---|---|---|---|
| Gly | Val | Arg | Val | Leu | Pro | Glu | Ile | Tyr | Ala | Pro | Asp | Arg | Asp | Glu | Pro | |
| | | | 1015 | | | | | 1020 | | | | | 1025 | | | |

| gac | acg | gac | aac | tcg | cgt | gtc | ggt | tac | gga | atc | ctg | gac | ctc | acg | atc | 3296 |
|---|---|---|---|---|---|---|---|---|---|---|---|---|---|---|---|---|
| Asp | Thr | Asp | Asn | Ser | Arg | Val | Gly | Tyr | Gly | Ile | Leu | Asp | Leu | Thr | Ile | |
| 1030 | | | | | 1035 | | | | | 1040 | | | | | 1045 | |

| acc | gac | cga | gac | atc | gag | gtg | ccg | gat | ctc | ttc | acc | atg | atc | tcg | att | 3344 |
|---|---|---|---|---|---|---|---|---|---|---|---|---|---|---|---|---|
| Thr | Asp | Arg | Asp | Ile | Glu | Val | Pro | Asp | Leu | Phe | Thr | Met | Ile | Ser | Ile | |
| | | | | 1050 | | | | | 1055 | | | | | 1060 | | |

| gaa | aac | aaa | act | ggg | gaa | ctt | gag | acc | gct | atg | gac | ttg | agg | ggg | tat | 3392 |
|---|---|---|---|---|---|---|---|---|---|---|---|---|---|---|---|---|
| Glu | Asn | Lys | Thr | Gly | Glu | Leu | Glu | Thr | Ala | Met | Asp | Leu | Arg | Gly | Tyr | |
| | | | 1065 | | | | | 1070 | | | | | 1075 | | | |

| tgg | ggc | act | tac | gaa | ata | ttc | att | gag | gcc | ttc | gac | cac | ggc | tac | ccg | 3440 |
|---|---|---|---|---|---|---|---|---|---|---|---|---|---|---|---|---|
| Trp | Gly | Thr | Tyr | Glu | Ile | Phe | Ile | Glu | Ala | Phe | Asp | His | Gly | Tyr | Pro | |
| | | | 1080 | | | | | 1085 | | | | | 1090 | | | |

| cag | cag | agg | tcc | aac | gag | acg | tac | acc | ctg | gtc | atc | cgc | ccc | tac | aac | 3488 |
|---|---|---|---|---|---|---|---|---|---|---|---|---|---|---|---|---|
| Gln | Gln | Arg | Ser | Asn | Glu | Thr | Tyr | Thr | Leu | Val | Ile | Arg | Pro | Tyr | Asn | |
| | | | 1095 | | | | | 1100 | | | | | 1105 | | | |

| ttc | cac | cac | cct | gtg | ttc | gtg | ttc | ccg | caa | ccc | gac | tcc | gtc | att | cgg | 3536 |
|---|---|---|---|---|---|---|---|---|---|---|---|---|---|---|---|---|
| Phe | His | His | Pro | Val | Phe | Val | Phe | Pro | Gln | Pro | Asp | Ser | Val | Ile | Arg | |
| 1110 | | | | | 1115 | | | | | 1120 | | | | | 1125 | |

| ctt | tct | agg | gag | cgc | gca | aca | gaa | ggc | ggc | gtt | ctg | gcg | acg | gct | gcc | 3584 |
|---|---|---|---|---|---|---|---|---|---|---|---|---|---|---|---|---|
| Leu | Ser | Arg | Glu | Arg | Ala | Thr | Glu | Gly | Gly | Val | Leu | Ala | Thr | Ala | Ala | |
| | | | | 1130 | | | | | 1135 | | | | | 1140 | | |

| aac | gag | ttc | ctg | gag | ccg | atc | tac | gcc | acc | gac | gag | gac | ggc | ctc | cac | 3632 |
|---|---|---|---|---|---|---|---|---|---|---|---|---|---|---|---|---|
| Asn | Glu | Phe | Leu | Glu | Pro | Ile | Tyr | Ala | Thr | Asp | Glu | Asp | Gly | Leu | His | |
| | | | | 1145 | | | | | 1150 | | | | | 1155 | | |

| gcg | ggc | agc | gtc | acg | ttc | cac | gtc | cag | gga | aat | gag | gag | gcc | gtt | cag | 3680 |
|---|---|---|---|---|---|---|---|---|---|---|---|---|---|---|---|---|
| Ala | Gly | Ser | Val | Thr | Phe | His | Val | Gln | Gly | Asn | Glu | Glu | Ala | Val | Gln | |
| | | | 1160 | | | | | 1165 | | | | | 1170 | | | |

| tac | ttt | gat | ata | act | gaa | gtg | gga | gca | gga | gaa | aat | agc | ggg | cag | ctt | 3728 |

```
Tyr Phe Asp Ile Thr Glu Val Gly Ala Gly Glu Asn Ser Gly Gln Leu
    1175                1180                1185 ata tta cgc cag ctt ttc cca gag caa atc aga caa ttc agg atc acg        3776
Ile Leu Arg Gln Leu Phe Pro Glu Gln Ile Arg Gln Phe Arg Ile Thr
1190                1195                1200                1205 atc cgg gcc acg gac ggc ggc acg gag ccc ggc ccg ctt tgg acc gac        3824
Ile Arg Ala Thr Asp Gly Gly Thr Glu Pro Gly Pro Leu Trp Thr Asp
                1210                1215                1220 gtc acg ttt tcg gtg gtc ttc gta ccc aca cag ggc gac cca gtg ttc        3872
Val Thr Phe Ser Val Val Phe Val Pro Thr Gln Gly Asp Pro Val Phe
            1225                1230                1235 agc gaa aat gca gct act gtc gcc ttc ttc gag ggt gaa gaa ggc ctc        3920
Ser Glu Asn Ala Ala Thr Val Ala Phe Phe Glu Gly Glu Glu Gly Leu
        1240                1245                1250 cgt gag agt ttt gag ctg ccg caa gca gaa gac ctt aaa aac cac ctc        3968
Arg Glu Ser Phe Glu Leu Pro Gln Ala Glu Asp Leu Lys Asn His Leu
    1255                1260                1265 tgc gaa gat gac tgc caa gat atc tac tac agg ttt att gac ggc aac        4016
Cys Glu Asp Asp Cys Gln Asp Ile Tyr Tyr Arg Phe Ile Asp Gly Asn
1270                1275                1280                1285 aac gag ggt ctt ttc gta ctg gac cag tca agc aac gtc atc tcc ctt        4064
Asn Glu Gly Leu Phe Val Leu Asp Gln Ser Ser Asn Val Ile Ser Leu
                1290                1295                1300 gcg cag gag ttg gac cgc gag gtg gcc acg tct tac acg ctg cac atc        4112
Ala Gln Glu Leu Asp Arg Glu Val Ala Thr Ser Tyr Thr Leu His Ile
            1305                1310                1315 gcg gcg agc aac tcg ccc gac gcc act ggg atc cct ctg cag act tcc        4160
Ala Ala Ser Asn Ser Pro Asp Ala Thr Gly Ile Pro Leu Gln Thr Ser
        1320                1325                1330 atc ctc gtt gtc acg gtc aat gta aga gaa gcg aac ccg cgc cca att        4208
Ile Leu Val Val Thr Val Asn Val Arg Glu Ala Asn Pro Arg Pro Ile
    1335                1340                1345 ttc gag cag gac ctt tac aca gcg ggc att tcg acg ttg gac agc att        4256
Phe Glu Gln Asp Leu Tyr Thr Ala Gly Ile Ser Thr Leu Asp Ser Ile
1350                1355                1360                1365 ggc cgg gaa ttg ctt act gtc agg gcg agc cac aca gaa gac gac acc        4304
Gly Arg Glu Leu Leu Thr Val Arg Ala Ser His Thr Glu Asp Asp Thr
                1370                1375                1380 atc acg tac acc ata gac cgt gcg agc atg cag ctg gac agc agc cta        4352
Ile Thr Tyr Thr Ile Asp Arg Ala Ser Met Gln Leu Asp Ser Ser Leu
            1385                1390                1395 gaa gcc gtg cgc gac tcg gcc ttc gcg ctg cat gcg acc acc ggc gtg        4400
Glu Ala Val Arg Asp Ser Ala Phe Ala Leu His Ala Thr Thr Gly Val
        1400                1405                1410 ctt tcg ctc aat atg cag ccc acc gct tcc atg cac ggc atg ttc gag        4448
Leu Ser Leu Asn Met Gln Pro Thr Ala Ser Met His Gly Met Phe Glu
    1415                1420                1425 ttc gac gtc atc gct acg gat aca gct tct gca atc gac aca gcc cgt        4496
Phe Asp Val Ile Ala Thr Asp Thr Ala Ser Ala Ile Asp Thr Ala Arg
1430                1435                1440                1445 gtg aaa gtc tac ctc atc tca tcg caa aac cgc gtg acc ttc att ttc        4544
Val Lys Val Tyr Leu Ile Ser Ser Gln Asn Arg Val Thr Phe Ile Phe
                1450                1455                1460 gat aac caa ctt gag acc gtt gag cag aac aga aat ttc ata gcg gcc        4592
Asp Asn Gln Leu Glu Thr Val Glu Gln Asn Arg Asn Phe Ile Ala Ala
            1465                1470                1475 acg ttc agc acc ggg ttc aac atg acg tgc aac atc gac cag gtg gtg        4640
Thr Phe Ser Thr Gly Phe Asn Met Thr Cys Asn Ile Asp Gln Val Val
        1480                1485                1490
```

-continued

```
ccg ttc agc gac agc agc ggc gtg gcg caa gac gac acc acc gag gtg      4688
Pro Phe Ser Asp Ser Ser Gly Val Ala Gln Asp Asp Thr Thr Glu Val
    1495                1500                1505 cgc gcg cac ttc atc cgg gac aac gtg ccc gtg cag gca caa gag gtc      4736
Arg Ala His Phe Ile Arg Asp Asn Val Pro Val Gln Ala Gln Glu Val
1510                1515                1520                1525 gag gcc gtc cgc agc gac acg gtg ctg ctg cgc acc atc cag ctg atg      4784
Glu Ala Val Arg Ser Asp Thr Val Leu Leu Arg Thr Ile Gln Leu Met
                1530                1535                1540 ctg agc acc aac agc ctg gtg ctg caa gac ctg gtg acg ggt gac act      4832
Leu Ser Thr Asn Ser Leu Val Leu Gln Asp Leu Val Thr Gly Asp Thr
            1545                1550                1555 ccg acg cta ggc gag gag tca atg cag atc gcc gtc tac gca cta gcc      4880
Pro Thr Leu Gly Glu Glu Ser Met Gln Ile Ala Val Tyr Ala Leu Ala
        1560                1565                1570 gcg ctc tcc gct gtg cta ggc ttc ctc tgc ctc gta ctg ctt ctc gca      4928
Ala Leu Ser Ala Val Leu Gly Phe Leu Cys Leu Val Leu Leu Leu Ala
    1575                1580                1585 ttg ttc tgt agg aca aga gca ctg aac cgg cag ctg caa gca ctc tcc      4976
Leu Phe Cys Arg Thr Arg Ala Leu Asn Arg Gln Leu Gln Ala Leu Ser
1590                1595                1600                1605 atg acg aag tac ggc tcg gtg gac tcc ggg ctg aac cgc gcc ggg ctg      5024
Met Thr Lys Tyr Gly Ser Val Asp Ser Gly Leu Asn Arg Ala Gly Leu
                1610                1615                1620 gcg ccg ggc acc aac aag cac gcc gtc gag ggc tcc aac ccc atg tgg      5072
Ala Pro Gly Thr Asn Lys His Ala Val Glu Gly Ser Asn Pro Met Trp
            1625                1630                1635 aac gag gcc atc cgc gcg ccc gac ttc gac gcc atc agt gac gcg agt      5120
Asn Glu Ala Ile Arg Ala Pro Asp Phe Asp Ala Ile Ser Asp Ala Ser
        1640                1645                1650 ggc gac tcc gac ctg atc ggc atc gag gac atg ccg caa ttc cgc gac      5168
Gly Asp Ser Asp Leu Ile Gly Ile Glu Asp Met Pro Gln Phe Arg Asp
    1655                1660                1665 gac tac ttc ccg ccc ggc gac aca gac tca agc agc ggc atc gtc ttg      5216
Asp Tyr Phe Pro Pro Gly Asp Thr Asp Ser Ser Ser Gly Ile Val Leu
1670                1675                1680                1685 cac atg ggc gaa gcc acg gac aac aag ccc gtg acc acg cat ggc aac      5264
His Met Gly Glu Ala Thr Asp Asn Lys Pro Val Thr Thr His Gly Asn
                1690                1695                1700 aac ttc ggg ttc aag tcc acc ccg tac ctg cca cag ccg cac cca aag      5312
Asn Phe Gly Phe Lys Ser Thr Pro Tyr Leu Pro Gln Pro His Pro Lys
            1705                1710                1715 taactgccag ggtataacct gtccagggtg cctacgccgc gcgaagtgcg cacacgcgtt   5372
tatcatcggg aaacattagc atgaagatac ctatgtacat attgtaaatt gtaacatatc   5432
tatttttata caaatatatt ttatttatat ttgctaaaaa aaaaaaaaaa aaaaaaaaaa   5492
ctcgag                                                              5498

<210> SEQ ID NO 2
<211> LENGTH: 1717
<212> TYPE: PRT
<213> ORGANISM: Ostrinia nubilalis
<400> SEQUENCE: 2

Met Gly Val Glu Arg Phe Phe Pro Ala Val Leu Leu Val Ser Leu Ala
 1               5                  10                  15

Ser Ala Ala Leu Ala Asn Gln Arg Cys Ser Tyr Ile Ile Ala Ile Pro
            20                  25                  30

Arg Pro Glu Thr Pro Glu Leu Pro Pro Ile Asp Tyr Glu Gly Lys Ser
```

-continued

```
                35                  40                  45
Trp Ser Glu Gln Pro Leu Ile Pro Gly Pro Thr Arg Glu Val Cys
         50                  55                  60
Met Glu Asn Phe Leu Pro Asp Gln Met Ile Gln Val Ile Tyr Met Glu
 65                  70                  75                  80
Glu Glu Ile Glu Gly Asp Val Ile Ile Ala Lys Leu Asn Tyr Gln Gly
                 85                  90                  95
Ser Asn Thr Pro Val Leu Ser Ile Met Ser Gly Gln Pro Arg Ala Gln
                100                 105                 110
Leu Gly Pro Glu Phe Arg Gln Asn Glu Ala Asp Gly Gln Trp Ser Leu
            115                 120                 125
Val Ile Thr Gln Arg Gln Asp Tyr Glu Thr Ala Thr Met Gln Ser Tyr
        130                 135                 140
Val Phe Ser Ile Gln Val Glu Gly Glu Ser Gln Ala Val Leu Val Ala
145                 150                 155                 160
Leu Glu Ile Val Asn Ile Asp Asp Asn Pro Pro Ile Leu Gln Val Val
                165                 170                 175
Ser Ala Cys Val Ile Pro Glu His Gly Glu Ala Arg Leu Thr Asp Cys
                180                 185                 190
Val Tyr Gln Val Ser Asp Arg Asp Gly Glu Ile Ser Thr Arg Phe Met
        195                 200                 205
Thr Phe Arg Val Asp Ser Ser Arg Ala Ala Asp Glu Ser Ile Phe Tyr
210                 215                 220
Met Val Gly Glu Tyr Asp Pro Ser Asp Trp Phe Asn Met Lys Met Thr
225                 230                 235                 240
Val Gly Ile Asn Ser Pro Leu Asn Phe Glu Thr Thr Gln Leu His Ile
                245                 250                 255
Phe Ser Val Thr Ala Ser Asp Ser Leu Pro Asn Asn His Thr Val Thr
                260                 265                 270
Met Met Val Gln Val Glu Asn Val Glu Ser Arg Pro Pro Arg Trp Val
        275                 280                 285
Glu Ile Phe Ser Val Gln Gln Phe Asp Glu Lys Thr Asn Gln Ser Phe
    290                 295                 300
Ser Leu Arg Ala Ile Asp Gly Asp Thr Gly Ile Asn Arg Ala Ile Asn
305                 310                 315                 320
Tyr Thr Leu Ile Arg Asp Asp Ala Asp Asp Phe Ser Leu Glu Val
                325                 330                 335
Ile Glu Asp Gly Ala Ile Leu His Val Thr Glu Ile Asp Arg Asp Lys
                340                 345                 350
Leu Glu Arg Glu Leu Phe Asn Leu Thr Ile Val Ala Tyr Lys Ser Thr
            355                 360                 365
Asp Ala Ser Phe Ala Thr Glu Ala His Ile Phe Ile Ile Val Asn Asp
        370                 375                 380
Val Asn Asp Gln Arg Pro Glu Pro Leu His Lys Glu Tyr Ser Ile Asp
385                 390                 395                 400
Ile Met Glu Glu Thr Pro Met Thr Leu Asn Phe Asn Glu Glu Phe Gly
                405                 410                 415
Phe His Asp Arg Asp Leu Gly Glu Asn Ala Gln Tyr Thr Val Glu Leu
                420                 425                 430
Glu Asp Val Phe Pro Pro Gly Ala Ala Ser Ala Phe Tyr Ile Ala Pro
            435                 440                 445
Gly Ser Gly Tyr Gln Arg Gln Thr Phe Ile Met Gly Thr Ile Asn His
450                 455                 460
```

-continued

```
Thr Met Leu Asp Tyr Glu Asp Val Ile Phe Gln Asn Ile Ile Ile Lys
465                 470                 475                 480

Val Lys Ala Val Asp Met Asn Asn Ala Ser His Val Gly Glu Ala Leu
                485                 490                 495

Val Tyr Val Asn Leu Ile Asn Trp Asn Asp Glu Leu Pro Ile Phe Glu
                500                 505                 510

Glu Ser Ser Tyr Ser Ala Ser Phe Lys Glu Thr Val Gly Ala Gly Phe
                515                 520                 525

Pro Val Ala Thr Val Leu Ala Leu Asp Arg Asp Ile Asp Asp Val Val
                530                 535                 540

Val His Ser Leu Met Gly Asn Ala Val Asp Tyr Leu Phe Ile Asp Glu
545                 550                 555                 560

Ser Thr Gly Glu Ile Phe Val Ser Met Asp Ala Phe Asp Tyr His
                565                 570                 575

Arg Gln Asn Thr Leu Phe Val Gln Val Arg Ala Asp Asp Thr Leu Gly
                580                 585                 590

Asp Gly Pro His Asn Thr Val Thr Thr Gln Leu Val Ile Glu Leu Glu
                595                 600                 605

Asp Val Asn Asn Thr Pro Pro Thr Leu Arg Leu Pro Arg Ser Thr Pro
610                 615                 620

Ser Val Glu Glu Asn Val Pro Glu Gly Tyr Glu Ile Ser Arg Glu Ile
625                 630                 635                 640

Thr Ala Thr Asp Pro Asp Thr Ser Ala Tyr Leu Trp Phe Glu Ile Asp
                645                 650                 655

Trp Asp Ser Thr Trp Ala Thr Lys Gln Gly Arg Glu Thr Asn Pro Thr
                660                 665                 670

Glu Tyr Val Gly Cys Ile Val Ile Glu Thr Ile Tyr Pro Thr Glu Gly
                675                 680                 685

Asn Arg Gly Ser Ala Ile Gly Arg Leu Val Val Gln Glu Ile Arg Asp
                690                 695                 700

Asn Val Thr Ile Asp Phe Glu Glu Phe Glu Met Leu Tyr Leu Thr Val
705                 710                 715                 720

Arg Val Arg Asp Leu Asn Thr Val Ile Gly Asp Tyr Asp Glu Ala
                725                 730                 735

Thr Phe Thr Ile Thr Ile Asp Met Asn Asp Asn Ala Pro Ile Phe
                740                 745                 750

Ala Asn Gly Thr Leu Thr Gln Thr Met Arg Val Arg Glu Leu Ala Ala
                755                 760                 765

Ser Gly Thr Leu Ile Gly Ser Val Leu Ala Thr Asp Ile Asp Gly Pro
770                 775                 780

Leu Tyr Asn Gln Val Arg Tyr Thr Ile Gln Pro Arg Asn Asn Thr Pro
785                 790                 795                 800

Glu Gly Leu Val Lys Ile Asp Phe Thr Thr Gly Gln Ile Glu Val Asp
                805                 810                 815

Ala Asn Glu Ala Ile Asp Ala Asp Glu Pro Trp Arg Phe Tyr Leu Tyr
                820                 825                 830

Tyr Thr Val Ile Ala Ser Asp Glu Cys Ser Leu Glu Asn Arg Thr Glu
                835                 840                 845

Cys Pro Pro Asp Ser Asn Tyr Phe Glu Val Pro Gly Asp Ile Glu Ile
850                 855                 860

Glu Ile Ile Asp Thr Asn Asn Lys Val Pro Glu Pro Leu Thr Glu Lys
865                 870                 875                 880
```

-continued

```
Phe Asn Thr Thr Val Tyr Val Trp Glu Asn Ala Thr Ser Gly Asp Glu
            885                 890                 895
Val Val Gln Leu Tyr Ser His Asp Arg Asp Arg Asp Glu Leu Tyr His
        900                 905                 910
Thr Val Arg Tyr Thr Met Asn Phe Ala Val Asn Pro Arg Leu Arg Asp
    915                 920                 925
Phe Phe Glu Val Asp Leu Asp Thr Gly Arg Leu Glu Val His Tyr Pro
930                 935                 940
Gly Asp Glu Lys Leu Asp Arg Asp Gly Asp Glu Pro Thr His Thr Ile
945                 950                 955                 960
Phe Val Asn Phe Ile Asp Asn Phe Phe Ser Asp Gly Asp Gly Arg Arg
            965                 970                 975
Asn Gln Asp Glu Val Glu Ile Phe Val Val Leu Leu Ala Val Asn Asp
        980                 985                 990
Asn Ala Pro Glu Met Pro Leu Pro Asp Glu Leu Arg Phe Asp Val Ser
    995                 1000                1005
Glu Gly Ala Val Ala Gly Val Arg Val Leu Pro Glu Ile Tyr Ala Pro
    1010                1015                1020
Asp Arg Asp Glu Pro Asp Thr Asp Asn Ser Arg Val Gly Tyr Gly Ile
1025                1030                1035                1040
Leu Asp Leu Thr Ile Thr Asp Arg Asp Ile Glu Val Pro Asp Leu Phe
            1045                1050                1055
Thr Met Ile Ser Ile Glu Asn Lys Thr Gly Glu Leu Glu Thr Ala Met
        1060                1065                1070
Asp Leu Arg Gly Tyr Trp Gly Thr Tyr Glu Ile Phe Ile Glu Ala Phe
    1075                1080                1085
Asp His Gly Tyr Pro Gln Gln Arg Ser Asn Glu Thr Tyr Thr Leu Val
    1090                1095                1100
Ile Arg Pro Tyr Asn Phe His His Pro Val Phe Val Phe Pro Gln Pro
1105                1110                1115                1120
Asp Ser Val Ile Arg Leu Ser Arg Glu Arg Ala Thr Glu Gly Gly Val
            1125                1130                1135
Leu Ala Thr Ala Ala Asn Glu Phe Leu Glu Pro Ile Tyr Ala Thr Asp
        1140                1145                1150
Glu Asp Gly Leu His Ala Gly Ser Val Thr Phe His Val Gln Gly Asn
    1155                1160                1165
Glu Glu Ala Val Gln Tyr Phe Asp Ile Thr Glu Val Gly Ala Gly Glu
    1170                1175                1180
Asn Ser Gly Gln Leu Ile Leu Arg Gln Leu Phe Pro Glu Gln Ile Arg
1185                1190                1195                1200
Gln Phe Arg Ile Thr Ile Arg Ala Thr Asp Gly Gly Thr Glu Pro Gly
            1205                1210                1215
Pro Leu Trp Thr Asp Val Thr Phe Ser Val Val Phe Val Pro Thr Gln
        1220                1225                1230
Gly Asp Pro Val Phe Ser Glu Asn Ala Ala Thr Val Ala Phe Phe Glu
    1235                1240                1245
Gly Glu Glu Gly Leu Arg Glu Ser Phe Glu Leu Pro Gln Ala Glu Asp
    1250                1255                1260
Leu Lys Asn His Leu Cys Glu Asp Asp Cys Gln Asp Ile Tyr Tyr Arg
1265                1270                1275                1280
Phe Ile Asp Gly Asn Asn Glu Gly Leu Phe Val Leu Asp Gln Ser Ser
            1285                1290                1295
Asn Val Ile Ser Leu Ala Gln Glu Leu Asp Arg Glu Val Ala Thr Ser
```

-continued

```
                1300                1305                1310
Tyr Thr Leu His Ile Ala Ala Ser Asn Ser Pro Asp Ala Thr Gly Ile
        1315                1320                1325

Pro Leu Gln Thr Ser Ile Leu Val Val Thr Val Asn Val Arg Glu Ala
        1330                1335                1340

Asn Pro Arg Pro Ile Phe Glu Gln Asp Leu Tyr Thr Ala Gly Ile Ser
1345                1350                1355                1360

Thr Leu Asp Ser Ile Gly Arg Glu Leu Leu Thr Val Arg Ala Ser His
            1365                1370                1375

Thr Glu Asp Asp Thr Ile Thr Tyr Thr Ile Asp Arg Ala Ser Met Gln
        1380                1385                1390

Leu Asp Ser Ser Leu Glu Ala Val Arg Asp Ser Ala Phe Ala Leu His
        1395                1400                1405

Ala Thr Thr Gly Val Leu Ser Leu Asn Met Gln Pro Thr Ala Ser Met
    1410                1415                1420

His Gly Met Phe Glu Phe Asp Val Ile Ala Thr Asp Thr Ala Ser Ala
1425                1430                1435                1440

Ile Asp Thr Ala Arg Val Lys Val Tyr Leu Ile Ser Ser Gln Asn Arg
            1445                1450                1455

Val Thr Phe Ile Phe Asp Asn Gln Leu Glu Thr Val Glu Gln Asn Arg
        1460                1465                1470

Asn Phe Ile Ala Ala Thr Phe Ser Thr Gly Phe Asn Met Thr Cys Asn
        1475                1480                1485

Ile Asp Gln Val Val Pro Phe Ser Asp Ser Ser Gly Val Ala Gln Asp
    1490                1495                1500

Asp Thr Thr Glu Val Arg Ala His Phe Ile Arg Asp Asn Val Pro Val
1505                1510                1515                1520

Gln Ala Gln Glu Val Glu Ala Val Arg Ser Asp Thr Val Leu Leu Arg
            1525                1530                1535

Thr Ile Gln Leu Met Leu Ser Thr Asn Ser Leu Val Leu Gln Asp Leu
        1540                1545                1550

Val Thr Gly Asp Thr Pro Thr Leu Gly Glu Glu Ser Met Gln Ile Ala
        1555                1560                1565

Val Tyr Ala Leu Ala Ala Leu Ser Ala Val Leu Gly Phe Leu Cys Leu
    1570                1575                1580

Val Leu Leu Leu Ala Leu Phe Cys Arg Thr Arg Ala Leu Asn Arg Gln
1585                1590                1595                1600

Leu Gln Ala Leu Ser Met Thr Lys Tyr Gly Ser Val Asp Ser Gly Leu
            1605                1610                1615

Asn Arg Ala Gly Leu Ala Pro Gly Thr Asn Lys His Ala Val Glu Gly
        1620                1625                1630

Ser Asn Pro Met Trp Asn Glu Ala Ile Arg Ala Pro Asp Phe Asp Ala
        1635                1640                1645

Ile Ser Asp Ala Ser Gly Asp Ser Asp Leu Ile Gly Ile Glu Asp Met
    1650                1655                1660

Pro Gln Phe Arg Asp Asp Tyr Phe Pro Pro Gly Asp Thr Asp Ser Ser
1665                1670                1675                1680

Ser Gly Ile Val Leu His Met Gly Glu Ala Thr Asp Asn Lys Pro Val
            1685                1690                1695

Thr Thr His Gly Asn Asn Phe Gly Phe Lys Ser Thr Pro Tyr Leu Pro
        1700                1705                1710

Gln Pro His Pro Lys
        1715
```

-continued

```
<210> SEQ ID NO 3
<211> LENGTH: 5527
<212> TYPE: DNA
<213> ORGANISM: Heliothis zea
<220> FEATURE:
<221> NAME/KEY: CDS
<222> LOCATION: (171)...(5360)

<400> SEQUENCE: 3
gtggattgtt gttctaaaaa cagaaaaaaa acgcagtttg aaaaaagtta tttttgtgat      60
atttgtgtaa agtgtagtgt taaataattt ggcattgctg taaaggatta aagagtgttc     120
caattgatca cccagaggtg gatcgaccag actagacaca gaactatgag atg gca       176
                                                         Met Ala
                                                          1 gtc gac gtg aga ata ttg acg gca gcg gtt ttc att atc gct gct cac      224
Val Asp Val Arg Ile Leu Thr Ala Ala Val Phe Ile Ile Ala Ala His
        5                  10                  15 ttg act ttc gcg caa gat tgt agc tac atg gta gca ata ccc aga cca      272
Leu Thr Phe Ala Gln Asp Cys Ser Tyr Met Val Ala Ile Pro Arg Pro
 20                  25                  30 gag cga cca gat ttt cca agt cta aat ttc gat gga ata cca tgg agt      320
Glu Arg Pro Asp Phe Pro Ser Leu Asn Phe Asp Gly Ile Pro Trp Ser
 35                  40                  45                  50 cgg tat ccc ctg ata cca gtg gag ggt aga gaa gat gtg tgc atg aac      368
Arg Tyr Pro Leu Ile Pro Val Glu Gly Arg Glu Asp Val Cys Met Asn
                55                  60                  65 gaa ttc cag cca gat gcc ttg aac cca gtt acc gtc atc ttc atg gag      416
Glu Phe Gln Pro Asp Ala Leu Asn Pro Val Thr Val Ile Phe Met Glu
             70                  75                  80 gag gag ata gaa ggg gat gtg gct atc gcg agg ctt aac tac cga ggt      464
Glu Glu Ile Glu Gly Asp Val Ala Ile Ala Arg Leu Asn Tyr Arg Gly
         85                  90                  95 acc aat act ccg acc att gta tct cca ttt agc ttt ggt act ttt aac      512
Thr Asn Thr Pro Thr Ile Val Ser Pro Phe Ser Phe Gly Thr Phe Asn
    100                 105                 110 atg ttg ggg ccg gtc ata cgt aga ata cct gag aat ggt ggc gac tgg      560
Met Leu Gly Pro Val Ile Arg Arg Ile Pro Glu Asn Gly Gly Asp Trp
115                 120                 125                 130 cat ctc gtc att aca cag aga cag gac tac gag acg cca ggt atg cag      608
His Leu Val Ile Thr Gln Arg Gln Asp Tyr Glu Thr Pro Gly Met Gln
                135                 140                 145 cag tac atc ttc gac gtg agg gta gac gat gaa ccg cta gtg gcc acg      656
Gln Tyr Ile Phe Asp Val Arg Val Asp Asp Glu Pro Leu Val Ala Thr
            150                 155                 160 gtg atg ctg ctc att gtc aac atc gat gac aac gat cct atc ata cag      704
Val Met Leu Leu Ile Val Asn Ile Asp Asp Asn Asp Pro Ile Ile Gln
        165                 170                 175 atg ttt gag cct tgt gat att cct gaa cgc ggt gaa aca ggc atc aca      752
Met Phe Glu Pro Cys Asp Ile Pro Glu Arg Gly Glu Thr Gly Ile Thr
    180                 185                 190 tca tgc aag tac acc gtg agc gat gct gac ggc gag atc agt aca cgt      800
Ser Cys Lys Tyr Thr Val Ser Asp Ala Asp Gly Glu Ile Ser Thr Arg
195                 200                 205                 210 ttc atg agg ttc gaa atc agc agc gat cga gac gat gac gaa tat ttc      848
Phe Met Arg Phe Glu Ile Ser Ser Asp Arg Asp Asp Asp Glu Tyr Phe
                215                 220                 225 gaa ctc gtc aga gaa aat ata caa gga caa tgg atg tat gtt cat atg      896
Glu Leu Val Arg Glu Asn Ile Gln Gly Gln Trp Met Tyr Val His Met
            230                 235                 240
```

```
aga gtt cac gtc aaa aaa cct ctt gat tat gag gaa aac ccg cta cat       944
Arg Val His Val Lys Lys Pro Leu Asp Tyr Glu Glu Asn Pro Leu His
        245                 250                 255 ttg ttt aga gtt aca gct tat gat tcc cta cca aac aca cat aca gtg       992
Leu Phe Arg Val Thr Ala Tyr Asp Ser Leu Pro Asn Thr His Thr Val
260                 265                 270 acg atg atg gtg caa gta gag aac gtt gag aac aga ccg ccg cga tgg      1040
Thr Met Met Val Gln Val Glu Asn Val Glu Asn Arg Pro Pro Arg Trp
275                 280                 285                 290 atg gag ata ttt gct gtc cag cag ttc gat gag aag acg gaa caa tcc      1088
Met Glu Ile Phe Ala Val Gln Gln Phe Asp Glu Lys Thr Glu Gln Ser
            295                 300                 305 ttt agg gtt cga gcc atc gat gga gat acg gga atc gat aaa cct att      1136
Phe Arg Val Arg Ala Ile Asp Gly Asp Thr Gly Ile Asp Lys Pro Ile
                310                 315                 320 ttc tat agg atc gaa act gaa aaa gga gag gaa gac ttg ttc agc att      1184
Phe Tyr Arg Ile Glu Thr Glu Lys Gly Glu Glu Asp Leu Phe Ser Ile
            325                 330                 335 caa acg ata gaa ggt ggt cga gaa ggc gct tgg ttt aac gtc gct cca      1232
Gln Thr Ile Glu Gly Gly Arg Glu Gly Ala Trp Phe Asn Val Ala Pro
                340                 345                 350 ata gac agg gac act cta gag aag gaa gtt ttc cac gtg tcc ata ata      1280
Ile Asp Arg Asp Thr Leu Glu Lys Glu Val Phe His Val Ser Ile Ile
355                 360                 365                 370 gcg tac aaa tat ggc gat aat gac gtg gaa ggc agt tcg tca ttc cag      1328
Ala Tyr Lys Tyr Gly Asp Asn Asp Val Glu Gly Ser Ser Ser Phe Gln
                    375                 380                 385 tcg aaa acc gat gtg gtc atc atc gtg aac gat gtc aat gat cag gcg      1376
Ser Lys Thr Asp Val Val Ile Ile Val Asn Asp Val Asn Asp Gln Ala
                390                 395                 400 ccg ctt cct ttc cgg gaa gag tac tcc att gaa att atg gag gaa act      1424
Pro Leu Pro Phe Arg Glu Glu Tyr Ser Ile Glu Ile Met Glu Glu Thr
            405                 410                 415 gcg atg acc ctg aat tta gaa gac ttt ggg ttc cat gat aga gat ctc      1472
Ala Met Thr Leu Asn Leu Glu Asp Phe Gly Phe His Asp Arg Asp Leu
420                 425                 430 ggt cct cac gca caa tac aca gta cac tta gag agc atc cat cct ccc      1520
Gly Pro His Ala Gln Tyr Thr Val His Leu Glu Ser Ile His Pro Pro
435                 440                 445                 450 cga gct cac gag gcg ttc tac ata gca ccg gag gtt ggc tac cag cgc      1568
Arg Ala His Glu Ala Phe Tyr Ile Ala Pro Glu Val Gly Tyr Gln Arg
                455                 460                 465 cag tcc ttc att atg ggc acg cag aac cat cac atg ctg gac ttc gaa      1616
Gln Ser Phe Ile Met Gly Thr Gln Asn His His Met Leu Asp Phe Glu
            470                 475                 480 gtg cca gag ttc cag aat ata caa ctg agg gcc gta gcg ata gac atg      1664
Val Pro Glu Phe Gln Asn Ile Gln Leu Arg Ala Val Ala Ile Asp Met
                485                 490                 495 gac gat ccc aaa tgg gtg ggt atc gcg ata atc aac att aaa ctg atc      1712
Asp Asp Pro Lys Trp Val Gly Ile Ala Ile Ile Asn Ile Lys Leu Ile
            500                 505                 510 aac tgg aac gat gag ctg ccg atg ttc gag agt gac gtg caa act gtc      1760
Asn Trp Asn Asp Glu Leu Pro Met Phe Glu Ser Asp Val Gln Thr Val
515                 520                 525                 530 agc ttc gat gag aca gag ggc gca ggc ttc tat gtg gcc act gtt gtg      1808
Ser Phe Asp Glu Thr Glu Gly Ala Gly Phe Tyr Val Ala Thr Val Val
                535                 540                 545 gcg aag gac cgg gat gtt ggt gat aaa gtc gaa cac tct cta atg ggt      1856
Ala Lys Asp Arg Asp Val Gly Asp Lys Val Glu His Ser Leu Met Gly
```

```
                550                 555                 560
aac gca gta agc tac ctg agg atc gac aag gaa acc ggc gag ata ttc    1904
Asn Ala Val Ser Tyr Leu Arg Ile Asp Lys Glu Thr Gly Glu Ile Phe
        565                 570                 575 gtc aca gaa aac gaa gca ttc aac tat cac agg cag aac gaa ctc ttt    1952
Val Thr Glu Asn Glu Ala Phe Asn Tyr His Arg Gln Asn Glu Leu Phe
580                 585                 590 gtg cag ata cca gct gac gac acg ctg ggc gag cct tac aac acc aac    2000
Val Gln Ile Pro Ala Asp Asp Thr Leu Gly Glu Pro Tyr Asn Thr Asn
595                 600                 605                 610 act act cag ttg gtg atc aag ctg cgg gac att aac aac acc cct cct    2048
Thr Thr Gln Leu Val Ile Lys Leu Arg Asp Ile Asn Asn Thr Pro Pro
                615                 620                 625 acg ctc agg ctg cct cgc gcc act cca tca gtg gaa gag aac gtg ccc    2096
Thr Leu Arg Leu Pro Arg Ala Thr Pro Ser Val Glu Glu Asn Val Pro
            630                 635                 640 gac ggg ttt gtg atc ccc acg cag ctg cac gcc acg gac ccc gac act    2144
Asp Gly Phe Val Ile Pro Thr Gln Leu His Ala Thr Asp Pro Asp Thr
        645                 650                 655 aca gct gag ctg cgc ttc gag atc gac tgg cag aac tcg tat gct acc    2192
Thr Ala Glu Leu Arg Phe Glu Ile Asp Trp Gln Asn Ser Tyr Ala Thr
    660                 665                 670 aag cag gga cgg aat act gac tct aag gag tat atc ggt tgt ata gaa    2240
Lys Gln Gly Arg Asn Thr Asp Ser Lys Glu Tyr Ile Gly Cys Ile Glu
675                 680                 685                 690 atc gag acg ata tac ccg aat ata aac cag cga ggc aac gcc atc ggc    2288
Ile Glu Thr Ile Tyr Pro Asn Ile Asn Gln Arg Gly Asn Ala Ile Gly
                695                 700                 705 cgc gtg gta gtg cga gag atc cgg gac ggc gtc acc ata gac tat gag    2336
Arg Val Val Val Arg Glu Ile Arg Asp Gly Val Thr Ile Asp Tyr Glu
            710                 715                 720 atg ttt gaa gtt cta tac ctc acc gtc att gtg agg gat ctc aac acc    2384
Met Phe Glu Val Leu Tyr Leu Thr Val Ile Val Arg Asp Leu Asn Thr
        725                 730                 735 gtt att gga gaa gac cat gat ata tcc aca ttc acg atc acg ata ata    2432
Val Ile Gly Glu Asp His Asp Ile Ser Thr Phe Thr Ile Thr Ile Ile
    740                 745                 750 gac atg aac gac aac cct ccc ctg tgg gtg gaa ggc acc ctg acg caa    2480
Asp Met Asn Asp Asn Pro Pro Leu Trp Val Glu Gly Thr Leu Thr Gln
755                 760                 765                 770 gag ttc cgt gtg cga gag gtg gca gcc tca gga gtt gtt ata gga tcc    2528
Glu Phe Arg Val Arg Glu Val Ala Ala Ser Gly Val Val Ile Gly Ser
                775                 780                 785 gta ctg gcc act gat atc gac gga ccg ctg tat aat caa gtg cgg tat    2576
Val Leu Ala Thr Asp Ile Asp Gly Pro Leu Tyr Asn Gln Val Arg Tyr
            790                 795                 800 act att act ccc aga cta gac act cca gaa gac cta gtg gac ata gac    2624
Thr Ile Thr Pro Arg Leu Asp Thr Pro Glu Asp Leu Val Asp Ile Asp
        805                 810                 815 ttc aac acg ggt cag atc tcc gta aag tta cac cag gct ata gac gcg    2672
Phe Asn Thr Gly Gln Ile Ser Val Lys Leu His Gln Ala Ile Asp Ala
    820                 825                 830 gac gag ccg ccg cgt cag aac ctc tac tac acc gtc ata gct agt gac    2720
Asp Glu Pro Pro Arg Gln Asn Leu Tyr Tyr Thr Val Ile Ala Ser Asp
835                 840                 845                 850 aag tgt gac ctc ctt act gtc act gag tgt ccg cct gac cct act tac    2768
Lys Cys Asp Leu Leu Thr Val Thr Glu Cys Pro Pro Asp Pro Thr Tyr
                855                 860                 865 ttt gag aca ccg gga gag att acc atc cac ata acg gac acg aac aac    2816
```

```
Phe Glu Thr Pro Gly Glu Ile Thr Ile His Ile Thr Asp Thr Asn Asn
            870                 875                 880 aag gtg cct caa gtg gaa gac gac aag ttc gag gcg acg gtg tac atc   2864
Lys Val Pro Gln Val Glu Asp Asp Lys Phe Glu Ala Thr Val Tyr Ile
        885                 890                 895 tac gag ggc gcg gac gat gga caa cat gtc gtg cag atc tac gcc agc   2912
Tyr Glu Gly Ala Asp Asp Gly Gln His Val Val Gln Ile Tyr Ala Ser
900                 905                 910 gat ctg gat aga gat gaa atc tac cac aaa gtg agc tac cag atc aac   2960
Asp Leu Asp Arg Asp Glu Ile Tyr His Lys Val Ser Tyr Gln Ile Asn
915                 920                 925                 930 tac gcg atc aac tct cgt ctc cgc gac ttc ttc gag atg gac ctg gag   3008
Tyr Ala Ile Asn Ser Arg Leu Arg Asp Phe Phe Glu Met Asp Leu Glu
                935                 940                 945 tcc ggc ctc gtg tac gtc aac aac acc gcc ggc gag ctg ctg gac agg   3056
Ser Gly Leu Val Tyr Val Asn Asn Thr Ala Gly Glu Leu Leu Asp Arg
            950                 955                 960 gac ggc gac gag ccc aca cat cgc atc ttc ttc aat gtc atc gat aac   3104
Asp Gly Asp Glu Pro Thr His Arg Ile Phe Phe Asn Val Ile Asp Asn
        965                 970                 975 ttc tat gga gaa gga gat ggc aac cgc aat cag aac gag aca caa gtg   3152
Phe Tyr Gly Glu Gly Asp Gly Asn Arg Asn Gln Asn Glu Thr Gln Val
980                 985                 990 tta gta gta ttg ctg gac atc aat gac aac tat ccg gaa ctg cct gaa   3200
Leu Val Val Leu Leu Asp Ile Asn Asp Asn Tyr Pro Glu Leu Pro Glu
995                 1000                1005                1010 act atc cca tgg gct atc tct gag agc tta gag ctg ggt gag cgt gta   3248
Thr Ile Pro Trp Ala Ile Ser Glu Ser Leu Glu Leu Gly Glu Arg Val
                1015                1020                1025 cag cca gaa atc ttt gcc cgg gac cgc gac gaa ccc gga aca gac aac   3296
Gln Pro Glu Ile Phe Ala Arg Asp Arg Asp Glu Pro Gly Thr Asp Asn
                1030                1035                1040 tcc cgc gtc gcc tat gcc atc aca ggc ctc gcc agc act gac cgg gac   3344
Ser Arg Val Ala Tyr Ala Ile Thr Gly Leu Ala Ser Thr Asp Arg Asp
            1045                1050                1055 ata caa gtg cct aat ctc ttc aac atg atc act ata gag agg gac agg   3392
Ile Gln Val Pro Asn Leu Phe Asn Met Ile Thr Ile Glu Arg Asp Arg
        1060                1065                1070 gga att gat cag aca gga ata ctt gag gca gct atg gat ttg aga ggc   3440
Gly Ile Asp Gln Thr Gly Ile Leu Glu Ala Ala Met Asp Leu Arg Gly
1075                1080                1085                1090 tat tgg ggc acc tat caa ata gat att cag gcg tat gac cat gga ata   3488
Tyr Trp Gly Thr Tyr Gln Ile Asp Ile Gln Ala Tyr Asp His Gly Ile
                1095                1100                1105 cct caa agg att tca aat cag aag tac ccg ctg gtg att aga cct tac   3536
Pro Gln Arg Ile Ser Asn Gln Lys Tyr Pro Leu Val Ile Arg Pro Tyr
            1110                1115                1120 aac ttc cac gac cca gtg ttc gtg ttc cct caa cct gga tcc act atc   3584
Asn Phe His Asp Pro Val Phe Val Phe Pro Gln Pro Gly Ser Thr Ile
        1125                1130                1135 aga ctg gca aag gag cga gca gta gtc aac ggt ata ctg gct aca gta   3632
Arg Leu Ala Lys Glu Arg Ala Val Val Asn Gly Ile Leu Ala Thr Val
        1140                1145                1150 gac ggc gaa ttt ctg gac aga atc gtt gcc acc gac gag gat ggt tta   3680
Asp Gly Glu Phe Leu Asp Arg Ile Val Ala Thr Asp Glu Asp Gly Leu
1155                1160                1165                1170 gaa gct gga ctt gtc aca ttc tct atc gcc gga gat gat gaa gat gct   3728
Glu Ala Gly Leu Val Thr Phe Ser Ile Ala Gly Asp Asp Glu Asp Ala
            1175                1180                1185
```

-continued

| | |
|---|---|
| cag ttc ttc gac gtg ttg aac gac gga gtg aac tcg ggt gct ctc acc<br>Gln Phe Phe Asp Val Leu Asn Asp Gly Val Asn Ser Gly Ala Leu Thr<br>          1190                      1195                      1200 | 3776 |
| ctc acg cgg ctc ttc cct gaa gag ttc cga gag ttc cag gtg acg att<br>Leu Thr Arg Leu Phe Pro Glu Glu Phe Arg Glu Phe Gln Val Thr Ile<br>          1205                      1210                      1215 | 3824 |
| cgt gct acg gac ggt gga act gag cct ggt cca agg agt acg gac tgc<br>Arg Ala Thr Asp Gly Gly Thr Glu Pro Gly Pro Arg Ser Thr Asp Cys<br>    1220                      1225                      1230 | 3872 |
| ttg gtg acc gta gtg ttt gta ccc acg cag gga gag ccc gtg ttc gag<br>Leu Val Thr Val Val Phe Val Pro Thr Gln Gly Glu Pro Val Phe Glu<br>1235                      1240                      1245                      1250 | 3920 |
| gat agg act tac acg gtt gct ttt gtt gaa aaa gat gag ggt atg tta<br>Asp Arg Thr Tyr Thr Val Ala Phe Val Glu Lys Asp Glu Gly Met Leu<br>                  1255                      1260                      1265 | 3968 |
| gag gag gcg gaa cta cct cgc gcc tca gac cca agg aac atc atg tgt<br>Glu Glu Ala Glu Leu Pro Arg Ala Ser Asp Pro Arg Asn Ile Met Cys<br>          1270                      1275                      1280 | 4016 |
| gaa gat gat tgt cac gac acc tat tac agc att gtt gga ggc aat tcg<br>Glu Asp Asp Cys His Asp Thr Tyr Tyr Ser Ile Val Gly Gly Asn Ser<br>    1285                      1290                      1295 | 4064 |
| ggt gaa cac ttc aca gta gac cct cgt acc aac gtg cta tcc ctg gtg<br>Gly Glu His Phe Thr Val Asp Pro Arg Thr Asn Val Leu Ser Leu Val<br>1300                      1305                      1310 | 4112 |
| aag ccg ctg gac cgc tcc gaa cag gag aca cac acc ctc atc att gga<br>Lys Pro Leu Asp Arg Ser Glu Gln Glu Thr His Thr Leu Ile Ile Gly<br>1315                      1320                      1325                      1330 | 4160 |
| gcc agc gac act ccc aac ccg gcc gcc gtc ctg cag gct tct aca ctc<br>Ala Ser Asp Thr Pro Asn Pro Ala Ala Val Leu Gln Ala Ser Thr Leu<br>                  1335                      1340                      1345 | 4208 |
| act gtc act gtt aat gtt cga gaa gcg aac ccg cga cca gtg ttc caa<br>Thr Val Thr Val Asn Val Arg Glu Ala Asn Pro Arg Pro Val Phe Gln<br>          1350                      1355                      1360 | 4256 |
| aga gca ctc tac aca gct ggc atc tct gct ggc gat ttc atc gaa aga<br>Arg Ala Leu Tyr Thr Ala Gly Ile Ser Ala Gly Asp Phe Ile Glu Arg<br>    1365                      1370                      1375 | 4304 |
| aat ctg ctg act tta gta gcg aca cat tca gaa gat ctg ccc atc act<br>Asn Leu Leu Thr Leu Val Ala Thr His Ser Glu Asp Leu Pro Ile Thr<br>1380                      1385                      1390 | 4352 |
| tac act ctg ata caa gag tcc atg gaa gca gac ccc aca ctc gaa gct<br>Tyr Thr Leu Ile Gln Glu Ser Met Glu Ala Asp Pro Thr Leu Glu Ala<br>1395                      1400                      1405                      1410 | 4400 |
| gtt cag gag tca gcc ttc atc ctc aac cct gag act gga gtc ctg tcc<br>Val Gln Glu Ser Ala Phe Ile Leu Asn Pro Glu Thr Gly Val Leu Ser<br>                  1415                      1420                      1425 | 4448 |
| ctc aac ttc cag cca acc gcc tcc atg cac ggc atg ttc gag ttc gaa<br>Leu Asn Phe Gln Pro Thr Ala Ser Met His Gly Met Phe Glu Phe Glu<br>                  1430                      1435                      1440 | 4496 |
| gtc aaa gcc act gat tca agg aca gaa act gcc cgc acg gaa gtg aag<br>Val Lys Ala Thr Asp Ser Arg Thr Glu Thr Ala Arg Thr Glu Val Lys<br>    1445                      1450                      1455 | 4544 |
| gtg tac ctg ata tca gac cgc aac cga gtg ttc ttc acg ttc aat aac<br>Val Tyr Leu Ile Ser Asp Arg Asn Arg Val Phe Phe Thr Phe Asn Asn<br>1460                      1465                      1470 | 4592 |
| cca ctg cct gaa gtc aca ccc cag gaa gat ttc ata gcg gag acg ttc<br>Pro Leu Pro Glu Val Thr Pro Gln Glu Asp Phe Ile Ala Glu Thr Phe<br>1475                      1480                      1485                      1490 | 4640 |
| acg gca ttc ttc ggc atg acg tgc aac atc gac cag tcg tgg tgg gcc<br>Thr Ala Phe Phe Gly Met Thr Cys Asn Ile Asp Gln Ser Trp Trp Ala<br>                  1495                      1500                      1505 | 4688 |

-continued

```
agc gat ccc gtc acc ggc gcc acc aag gac gac cag act gaa gtc agg      4736
Ser Asp Pro Val Thr Gly Ala Thr Lys Asp Asp Gln Thr Glu Val Arg
            1510                1515                1520 gct cat ttc atc agg gac gac ctt ccc gtg cct gct gag gag att gaa      4784
Ala His Phe Ile Arg Asp Asp Leu Pro Val Pro Ala Glu Glu Ile Glu
        1525                1530                1535 cag tta cgc ggt aac cca act cta gta aat agc atc caa cga gcc ctg      4832
Gln Leu Arg Gly Asn Pro Thr Leu Val Asn Ser Ile Gln Arg Ala Leu
    1540                1545                1550 gag gaa cag aac ctg cag cta gcc gac ctg ttc acg ggc gag acg ccc      4880
Glu Glu Gln Asn Leu Gln Leu Ala Asp Leu Phe Thr Gly Glu Thr Pro
1555                1560                1565                1570 atc ctc ggc ggc gac gcg cag gct cga gcc ctg tac gcg ctg gcg gcg      4928
Ile Leu Gly Gly Asp Ala Gln Ala Arg Ala Leu Tyr Ala Leu Ala Ala
                1575                1580                1585 gtg gcg gcg gca ctc gcg ctg att gtt gtt gtg ctg ctg att gtg ttc      4976
Val Ala Ala Ala Leu Ala Leu Ile Val Val Val Leu Leu Ile Val Phe
            1590                1595                1600 ttt gtt agg act agg act ctg aac cgg cgc ttg caa gct ctg tcc atg      5024
Phe Val Arg Thr Arg Thr Leu Asn Arg Arg Leu Gln Ala Leu Ser Met
        1605                1610                1615 acc aag tac agt tcg caa gac tct ggg ttg aac cgc gtg ggt ttg gcg      5072
Thr Lys Tyr Ser Ser Gln Asp Ser Gly Leu Asn Arg Val Gly Leu Ala
    1620                1625                1630 gcg ccg ggc acc aat aag cac gct gtc gag ggc tcc aac ccc atc tgg      5120
Ala Pro Gly Thr Asn Lys His Ala Val Glu Gly Ser Asn Pro Ile Trp
1635                1640                1645                1650 aat gaa acg ttg aag gct ccg gac ttt gac gct ctt agc gag cag tcg      5168
Asn Glu Thr Leu Lys Ala Pro Asp Phe Asp Ala Leu Ser Glu Gln Ser
                1655                1660                1665 tac gac tca gac cta atc ggc atc gaa gac ttg ccg cag ttc agg aac      5216
Tyr Asp Ser Asp Leu Ile Gly Ile Glu Asp Leu Pro Gln Phe Arg Asn
            1670                1675                1680 gac tac ttc cca cct gag gag ggc agc tcc atg cga gga gtc gtc aat      5264
Asp Tyr Phe Pro Pro Glu Glu Gly Ser Ser Met Arg Gly Val Val Asn
        1685                1690                1695 gaa cac gtg cct gaa tca ata gca aac cat aac aac aac ttc ggg ttt      5312
Glu His Val Pro Glu Ser Ile Ala Asn His Asn Asn Asn Phe Gly Phe
    1700                1705                1710 aac tct act ccc ttc agc cca gag ttc gcg aac acg cag ttc aga aga      5360
Asn Ser Thr Pro Phe Ser Pro Glu Phe Ala Asn Thr Gln Phe Arg Arg
1715                1720                1725                1730 taaaatatta aagcatttta aattataata ttatgtaccg gtgaaatacc atacttatat    5420
ttacctaagt atatattaaa gtgagattaa gtaagatact cgtattaatt aagagcattt    5480
atttttttaa atacaaaaca attaaactaa aaaaaaaaaa aaaaaa                   5527

<210> SEQ ID NO 4
<211> LENGTH: 1730
<212> TYPE: PRT
<213> ORGANISM: Heliothis zea

<400> SEQUENCE: 4

Met Ala Val Asp Val Arg Ile Leu Thr Ala Ala Val Phe Ile Ile Ala
  1               5                  10                  15

Ala His Leu Thr Phe Ala Gln Asp Cys Ser Tyr Met Val Ala Ile Pro
             20                  25                  30

Arg Pro Glu Arg Pro Asp Phe Pro Ser Leu Asn Phe Asp Gly Ile Pro
         35                  40                  45
```

```
Trp Ser Arg Tyr Pro Leu Ile Pro Val Glu Gly Arg Glu Asp Val Cys
     50                  55                  60

Met Asn Glu Phe Gln Pro Asp Ala Leu Asn Pro Val Thr Val Ile Phe
 65                  70                  75                  80

Met Glu Glu Glu Ile Glu Gly Asp Val Ala Ile Ala Arg Leu Asn Tyr
                     85                  90                  95

Arg Gly Thr Asn Thr Pro Thr Ile Val Ser Pro Phe Ser Phe Gly Thr
                 100                 105                 110

Phe Asn Met Leu Gly Pro Val Ile Arg Arg Ile Pro Glu Asn Gly Gly
             115                 120                 125

Asp Trp His Leu Val Ile Thr Gln Arg Gln Asp Tyr Glu Thr Pro Gly
         130                 135                 140

Met Gln Gln Tyr Ile Phe Asp Val Arg Val Asp Glu Pro Leu Val
145                 150                 155                 160

Ala Thr Val Met Leu Leu Ile Val Asn Ile Asp Asp Asn Asp Pro Ile
                 165                 170                 175

Ile Gln Met Phe Glu Pro Cys Asp Ile Pro Glu Arg Gly Glu Thr Gly
             180                 185                 190

Ile Thr Ser Cys Lys Tyr Thr Val Ser Asp Ala Asp Gly Glu Ile Ser
         195                 200                 205

Thr Arg Phe Met Arg Phe Glu Ile Ser Ser Asp Arg Asp Asp Glu
     210                 215                 220

Tyr Phe Glu Leu Val Arg Glu Asn Ile Gln Gly Gln Trp Met Tyr Val
225                 230                 235                 240

His Met Arg Val His Val Lys Lys Pro Leu Asp Tyr Glu Glu Asn Pro
                 245                 250                 255

Leu His Leu Phe Arg Val Thr Ala Tyr Asp Ser Leu Pro Asn Thr His
             260                 265                 270

Thr Val Thr Met Met Val Gln Val Glu Asn Val Glu Asn Arg Pro Pro
         275                 280                 285

Arg Trp Met Glu Ile Phe Ala Val Gln Gln Phe Asp Glu Lys Thr Glu
     290                 295                 300

Gln Ser Phe Arg Val Arg Ala Ile Asp Gly Asp Thr Gly Ile Asp Lys
305                 310                 315                 320

Pro Ile Phe Tyr Arg Ile Glu Thr Glu Lys Gly Glu Glu Asp Leu Phe
                 325                 330                 335

Ser Ile Gln Thr Ile Glu Gly Gly Arg Glu Gly Ala Trp Phe Asn Val
             340                 345                 350

Ala Pro Ile Asp Arg Asp Thr Leu Glu Lys Glu Val Phe His Val Ser
         355                 360                 365

Ile Ile Ala Tyr Lys Tyr Gly Asp Asn Asp Val Glu Gly Ser Ser Ser
     370                 375                 380

Phe Gln Ser Lys Thr Asp Val Val Ile Val Asn Asp Val Asn Asp
385                 390                 395                 400

Gln Ala Pro Leu Pro Phe Arg Glu Glu Tyr Ser Ile Glu Ile Met Glu
                 405                 410                 415

Glu Thr Ala Met Thr Leu Asn Leu Glu Asp Phe Gly Phe His Asp Arg
             420                 425                 430

Asp Leu Gly Pro His Ala Gln Tyr Thr Val His Leu Glu Ser Ile His
         435                 440                 445

Pro Pro Arg Ala His Glu Ala Phe Tyr Ile Ala Pro Glu Val Gly Tyr
     450                 455                 460
```

-continued

```
Gln Arg Gln Ser Phe Ile Met Gly Thr Gln Asn His His Met Leu Asp
465                 470                 475                 480

Phe Glu Val Pro Glu Phe Gln Asn Ile Gln Leu Arg Ala Val Ala Ile
            485                 490                 495

Asp Met Asp Asp Pro Lys Trp Val Gly Ile Ala Ile Ile Asn Ile Lys
        500                 505                 510

Leu Ile Asn Trp Asn Asp Glu Leu Pro Met Phe Glu Ser Asp Val Gln
    515                 520                 525

Thr Val Ser Phe Asp Glu Thr Glu Gly Ala Gly Phe Tyr Val Ala Thr
530                 535                 540

Val Val Ala Lys Asp Arg Asp Val Gly Asp Lys Val Glu His Ser Leu
545                 550                 555                 560

Met Gly Asn Ala Val Ser Tyr Leu Arg Ile Asp Lys Glu Thr Gly Glu
            565                 570                 575

Ile Phe Val Thr Glu Asn Glu Ala Phe Asn Tyr His Arg Gln Asn Glu
        580                 585                 590

Leu Phe Val Gln Ile Pro Ala Asp Asp Thr Leu Gly Glu Pro Tyr Asn
    595                 600                 605

Thr Asn Thr Thr Gln Leu Val Ile Lys Leu Arg Asp Ile Asn Asn Thr
610                 615                 620

Pro Pro Thr Leu Arg Leu Pro Arg Ala Thr Pro Ser Val Glu Glu Asn
625                 630                 635                 640

Val Pro Asp Gly Phe Val Ile Pro Thr Gln Leu His Ala Thr Asp Pro
            645                 650                 655

Asp Thr Thr Ala Glu Leu Arg Phe Glu Ile Asp Trp Gln Asn Ser Tyr
        660                 665                 670

Ala Thr Lys Gln Gly Arg Asn Thr Asp Ser Lys Glu Tyr Ile Gly Cys
    675                 680                 685

Ile Glu Ile Glu Thr Ile Tyr Pro Asn Ile Asn Gln Arg Gly Asn Ala
690                 695                 700

Ile Gly Arg Val Val Arg Glu Ile Arg Asp Gly Val Thr Ile Asp
705                 710                 715                 720

Tyr Glu Met Phe Glu Val Leu Tyr Leu Thr Val Ile Val Arg Asp Leu
            725                 730                 735

Asn Thr Val Ile Gly Glu Asp His Asp Ile Ser Thr Phe Thr Ile Thr
        740                 745                 750

Ile Ile Asp Met Asn Asp Asn Pro Pro Leu Trp Val Glu Gly Thr Leu
    755                 760                 765

Thr Gln Glu Phe Arg Val Arg Glu Val Ala Ala Ser Gly Val Val Ile
770                 775                 780

Gly Ser Val Leu Ala Thr Asp Ile Asp Gly Pro Leu Tyr Asn Gln Val
785                 790                 795                 800

Arg Tyr Thr Ile Thr Pro Arg Leu Asp Thr Pro Glu Asp Leu Val Asp
            805                 810                 815

Ile Asp Phe Asn Thr Gly Gln Ile Ser Val Lys Leu His Gln Ala Ile
        820                 825                 830

Asp Ala Asp Glu Pro Pro Arg Gln Asn Leu Tyr Tyr Thr Val Ile Ala
    835                 840                 845

Ser Asp Lys Cys Asp Leu Leu Thr Val Thr Glu Cys Pro Pro Asp Pro
850                 855                 860

Thr Tyr Phe Glu Thr Pro Gly Glu Ile Thr Ile His Ile Thr Asp Thr
865                 870                 875                 880

Asn Asn Lys Val Pro Gln Val Glu Asp Asp Lys Phe Glu Ala Thr Val
```

-continued

```
                885                 890                 895
Tyr Ile Tyr Glu Gly Ala Asp Asp Gly Gln His Val Val Gln Ile Tyr
            900                 905                 910
Ala Ser Asp Leu Asp Arg Asp Glu Ile Tyr His Lys Val Ser Tyr Gln
            915                 920                 925
Ile Asn Tyr Ala Ile Asn Ser Arg Leu Arg Asp Phe Phe Glu Met Asp
            930                 935                 940
Leu Glu Ser Gly Leu Val Tyr Val Asn Asn Thr Ala Gly Glu Leu Leu
945                 950                 955                 960
Asp Arg Asp Gly Asp Glu Pro Thr His Arg Ile Phe Phe Asn Val Ile
                965                 970                 975
Asp Asn Phe Tyr Gly Glu Gly Asp Gly Asn Arg Asn Gln Asn Glu Thr
            980                 985                 990
Gln Val Leu Val Val Leu Leu Asp Ile Asn Asp Asn Tyr Pro Glu Leu
            995                 1000                1005
Pro Glu Thr Ile Pro Trp Ala Ile Ser Glu Ser Leu Glu Leu Gly Glu
            1010                1015                1020
Arg Val Gln Pro Glu Ile Phe Ala Arg Asp Arg Asp Glu Pro Gly Thr
1025                1030                1035                1040
Asp Asn Ser Arg Val Ala Tyr Ala Ile Thr Gly Leu Ala Ser Thr Asp
                1045                1050                1055
Arg Asp Ile Gln Val Pro Asn Leu Phe Asn Met Ile Thr Ile Glu Arg
            1060                1065                1070
Asp Arg Gly Ile Asp Gln Thr Gly Ile Leu Glu Ala Ala Met Asp Leu
            1075                1080                1085
Arg Gly Tyr Trp Gly Thr Tyr Gln Ile Asp Ile Gln Ala Tyr Asp His
            1090                1095                1100
Gly Ile Pro Gln Arg Ile Ser Asn Gln Lys Tyr Pro Leu Val Ile Arg
1105                1110                1115                1120
Pro Tyr Asn Phe His Asp Pro Val Phe Val Phe Pro Gln Pro Gly Ser
                1125                1130                1135
Thr Ile Arg Leu Ala Lys Glu Arg Ala Val Val Asn Gly Ile Leu Ala
            1140                1145                1150
Thr Val Asp Gly Glu Phe Leu Asp Arg Ile Val Ala Thr Asp Glu Asp
            1155                1160                1165
Gly Leu Glu Ala Gly Leu Val Thr Phe Ser Ile Ala Gly Asp Asp Glu
            1170                1175                1180
Asp Ala Gln Phe Phe Asp Val Leu Asn Asp Gly Val Asn Ser Gly Ala
1185                1190                1195                1200
Leu Thr Leu Thr Arg Leu Phe Pro Glu Glu Phe Arg Glu Phe Gln Val
            1205                1210                1215
Thr Ile Arg Ala Thr Asp Gly Gly Thr Glu Pro Gly Pro Arg Ser Thr
            1220                1225                1230
Asp Cys Leu Val Thr Val Val Phe Val Pro Thr Gln Gly Glu Pro Val
            1235                1240                1245
Phe Glu Asp Arg Thr Tyr Thr Val Ala Phe Val Glu Lys Asp Glu Gly
            1250                1255                1260
Met Leu Glu Glu Ala Glu Leu Pro Arg Ala Ser Asp Pro Arg Asn Ile
1265                1270                1275                1280
Met Cys Glu Asp Asp Cys His Asp Thr Tyr Tyr Ser Ile Val Gly Gly
                1285                1290                1295
Asn Ser Gly Glu His Phe Thr Val Asp Pro Arg Thr Asn Val Leu Ser
            1300                1305                1310
```

```
Leu Val Lys Pro Leu Asp Arg Ser Glu Gln Glu Thr His Thr Leu Ile
        1315                1320                1325

Ile Gly Ala Ser Asp Thr Pro Asn Pro Ala Ala Val Leu Gln Ala Ser
        1330                1335                1340

Thr Leu Thr Val Thr Val Asn Val Arg Glu Ala Asn Pro Arg Pro Val
1345                1350                1355                1360

Phe Gln Arg Ala Leu Tyr Thr Ala Gly Ile Ser Ala Gly Asp Phe Ile
        1365                1370                1375

Glu Arg Asn Leu Leu Thr Leu Val Ala Thr His Ser Glu Asp Leu Pro
        1380                1385                1390

Ile Thr Tyr Thr Leu Ile Gln Glu Ser Met Glu Ala Asp Pro Thr Leu
        1395                1400                1405

Glu Ala Val Gln Glu Ser Ala Phe Ile Leu Asn Pro Glu Thr Gly Val
        1410                1415                1420

Leu Ser Leu Asn Phe Gln Pro Thr Ala Ser Met His Gly Met Phe Glu
1425                1430                1435                1440

Phe Glu Val Lys Ala Thr Asp Ser Arg Thr Glu Thr Ala Arg Thr Glu
        1445                1450                1455

Val Lys Val Tyr Leu Ile Ser Asp Arg Asn Arg Val Phe Phe Thr Phe
        1460                1465                1470

Asn Asn Pro Leu Pro Glu Val Thr Pro Gln Glu Asp Phe Ile Ala Glu
        1475                1480                1485

Thr Phe Thr Ala Phe Phe Gly Met Thr Cys Asn Ile Asp Gln Ser Trp
        1490                1495                1500

Trp Ala Ser Asp Pro Val Thr Gly Ala Thr Lys Asp Asp Gln Thr Glu
1505                1510                1515                1520

Val Arg Ala His Phe Ile Arg Asp Asp Leu Pro Val Pro Ala Glu Glu
        1525                1530                1535

Ile Glu Gln Leu Arg Gly Asn Pro Thr Leu Val Asn Ser Ile Gln Arg
        1540                1545                1550

Ala Leu Glu Glu Gln Asn Leu Gln Leu Ala Asp Leu Phe Thr Gly Glu
        1555                1560                1565

Thr Pro Ile Leu Gly Gly Asp Ala Gln Ala Arg Ala Leu Tyr Ala Leu
        1570                1575                1580

Ala Ala Val Ala Ala Ala Leu Ala Leu Ile Val Val Val Leu Leu Ile
1585                1590                1595                1600

Val Phe Phe Val Arg Thr Arg Thr Leu Asn Arg Arg Leu Gln Ala Leu
        1605                1610                1615

Ser Met Thr Lys Tyr Ser Ser Gln Asp Ser Gly Leu Asn Arg Val Gly
        1620                1625                1630

Leu Ala Ala Pro Gly Thr Asn Lys His Ala Val Glu Gly Ser Asn Pro
        1635                1640                1645

Ile Trp Asn Glu Thr Leu Lys Ala Pro Asp Phe Asp Ala Leu Ser Glu
        1650                1655                1660

Gln Ser Tyr Asp Ser Asp Leu Ile Gly Ile Glu Asp Leu Pro Gln Phe
1665                1670                1675                1680

Arg Asn Asp Tyr Phe Pro Pro Glu Gly Ser Ser Met Arg Gly Val
        1685                1690                1695

Val Asn Glu His Val Pro Glu Ser Ile Ala Asn His Asn Asn Asn Phe
        1700                1705                1710

Gly Phe Asn Ser Thr Pro Phe Ser Pro Glu Phe Ala Asn Thr Gln Phe
        1715                1720                1725
```

Arg Arg
    1730

<210> SEQ ID NO 5
<211> LENGTH: 5592
<212> TYPE: DNA
<213> ORGANISM: Spodoptera frugiperda
<220> FEATURE:
<221> NAME/KEY: CDS
<222> LOCATION: (162)...(5363)

<400> SEQUENCE: 5

| | |
|---|---:|
| gacattctgt ggtgaaaaca ttttttattt attttttttct agtggtttgt gggtacagtg | 60 |
| taaacatttt ggaatattgt taaagatttc ggaatattgt taaagtattg acagataaag | 120 |
| ctgtaacatc actagagaag tgagaactgc aagatcatga g atg gcg gtc gat gtg | 176 |

Met Ala Val Asp Val
                                                1               5

| | |
|---|---:|
| cga ata ctg aca gca aca ttg ctg gta ctc acc act gct aca gca cag<br>Arg Ile Leu Thr Ala Thr Leu Leu Val Leu Thr Thr Ala Thr Ala Gln<br>          10                  15                  20 | 224 |
| cga gat cga tgt ggc tac atg gta gaa ata ccc aga cca gac agg cct<br>Arg Asp Arg Cys Gly Tyr Met Val Glu Ile Pro Arg Pro Asp Arg Pro<br>      25                  30                  35 | 272 |
| gac ttc cca cct caa aat ttt gac ggt tta aca tgg gct cag cag cca<br>Asp Phe Pro Pro Gln Asn Phe Asp Gly Leu Thr Trp Ala Gln Gln Pro<br>  40                  45                  50 | 320 |
| cta tta cca gct gag gat cga gaa gag gtc tgc ctc aat gac tat gaa<br>Leu Leu Pro Ala Glu Asp Arg Glu Glu Val Cys Leu Asn Asp Tyr Glu<br>55                  60                  65 | 368 |
| cct gat ccc tgg agc aac aac cat ggt gac cag aga att tac atg gag<br>Pro Asp Pro Trp Ser Asn Asn His Gly Asp Gln Arg Ile Tyr Met Glu<br>              70                  75                  80                  85 | 416 |
| gag gag atc gaa ggt ccc gta gtc att gcg aaa att aac tac caa gga<br>Glu Glu Ile Glu Gly Pro Val Val Ile Ala Lys Ile Asn Tyr Gln Gly<br>                  90                  95                 100 | 464 |
| aac acc cct cct caa ata aga tta cct ttt cgt gtt ggt gca gcc cac<br>Asn Thr Pro Pro Gln Ile Arg Leu Pro Phe Arg Val Gly Ala Ala His<br>             105                 110                 115 | 512 |
| atg ctt gga gca gaa att cgt gaa tat cct gac gca act gga gac tgg<br>Met Leu Gly Ala Glu Ile Arg Glu Tyr Pro Asp Ala Thr Gly Asp Trp<br>         120                 125                 130 | 560 |
| tat ctt gta att act caa agg cag gac tat gaa act cct gat atg cag<br>Tyr Leu Val Ile Thr Gln Arg Gln Asp Tyr Glu Thr Pro Asp Met Gln<br>     135                 140                 145 | 608 |
| aga tac acg ttc gat gtg agt gtg gaa ggc cag tcg ctg gtt gta acg<br>Arg Tyr Thr Phe Asp Val Ser Val Glu Gly Gln Ser Leu Val Val Thr<br>150                 155                 160                 165 | 656 |
| gtg agg ctg gat att gtg aac atc gac gac aat gcg ccc atc att gag<br>Val Arg Leu Asp Ile Val Asn Ile Asp Asp Asn Ala Pro Ile Ile Glu<br>                 170                 175                 180 | 704 |
| atg tta gag cct tgc aac tta ccg gaa ctt gtt gaa ccc cat gtt aca<br>Met Leu Glu Pro Cys Asn Leu Pro Glu Leu Val Glu Pro His Val Thr<br>             185                 190                 195 | 752 |
| gaa tgt aaa tat atc gtg tcc gac gca gac ggt ctg atc agt aca agt<br>Glu Cys Lys Tyr Ile Val Ser Asp Ala Asp Gly Leu Ile Ser Thr Ser<br>         200                 205                 210 | 800 |
| gtt atg agt tat cat ata gac agc gag aga gga gac gaa aaa gta ttc<br>Val Met Ser Tyr His Ile Asp Ser Glu Arg Gly Asp Glu Lys Val Phe<br>     215                 220                 225 | 848 |
| gaa ctg atc aga aaa gat tat ccg ggc gat tgg acg aag gtg tat atg | 896 |

```
Glu Leu Ile Arg Lys Asp Tyr Pro Gly Asp Trp Thr Lys Val Tyr Met
230             235             240             245 gtt ctt gaa ttg aaa aaa tct ctt gat tac gaa gag aat cct cta cac      944
Val Leu Glu Leu Lys Lys Ser Leu Asp Tyr Glu Glu Asn Pro Leu His
            250             255             260 ata ttc aga gtc acg gct tct gat tcc tta cca aac aat agg acc gtg      992
Ile Phe Arg Val Thr Ala Ser Asp Ser Leu Pro Asn Asn Arg Thr Val
                265             270             275 gtc atg atg gtt gaa gta gag aac gtg gaa cat aga aat cct cgg tgg     1040
Val Met Met Val Glu Val Glu Asn Val Glu His Arg Asn Pro Arg Trp
            280             285             290 atg gag atc ttt gct gtg caa cag ttt gat gaa aaa cag gcg aaa tcg     1088
Met Glu Ile Phe Ala Val Gln Gln Phe Asp Glu Lys Gln Ala Lys Ser
295             300             305 ttc aca gtg cga gct att gat ggc gac acg gga atc aat aaa cct ata     1136
Phe Thr Val Arg Ala Ile Asp Gly Asp Thr Gly Ile Asn Lys Pro Ile
310             315             320             325 ttc tat cgt ata gaa act gaa gat gaa gac aaa gag ttc ttc agc att     1184
Phe Tyr Arg Ile Glu Thr Glu Asp Glu Asp Lys Glu Phe Phe Ser Ile
            330             335             340 gag aac ata ggg gaa ggc aga gac ggt gcc aga ttc cac gtg gct cct     1232
Glu Asn Ile Gly Glu Gly Arg Asp Gly Ala Arg Phe His Val Ala Pro
                345             350             355 ata gac aga gac tac ctg aaa agg gat atg ttt cat ata aga ata att     1280
Ile Asp Arg Asp Tyr Leu Lys Arg Asp Met Phe His Ile Arg Ile Ile
            360             365             370 gca tat aaa caa ggt gat aat gac aaa gaa ggt gaa tca tcg ttc gag     1328
Ala Tyr Lys Gln Gly Asp Asn Asp Lys Glu Gly Glu Ser Ser Phe Glu
375             380             385 acc tca gca aat gtg acg att ata att aac gat ata aat gat cag agg     1376
Thr Ser Ala Asn Val Thr Ile Ile Ile Asn Asp Ile Asn Asp Gln Arg
390             395             400             405 cca gaa ccc ttc cat aaa gaa tac acg atc tcc ata atg gaa gaa act     1424
Pro Glu Pro Phe His Lys Glu Tyr Thr Ile Ser Ile Met Glu Glu Thr
            410             415             420 gcg atg acc tta gat ttg caa gag ttt ggt ttc cat gac cgt gac att     1472
Ala Met Thr Leu Asp Leu Gln Glu Phe Gly Phe His Asp Arg Asp Ile
                425             430             435 ggt ccc cac gct cag tac gac gtt cac tta gag agt ata cag cca gag     1520
Gly Pro His Ala Gln Tyr Asp Val His Leu Glu Ser Ile Gln Pro Glu
            440             445             450 ggg gcc cat acc gct ttc tac atc gcc cct gaa gaa ggt tac cag gcc     1568
Gly Ala His Thr Ala Phe Tyr Ile Ala Pro Glu Glu Gly Tyr Gln Ala
455             460             465 cag tct ttc acc ata ggt act aga atc cat aac atg ttg gat tat gaa     1616
Gln Ser Phe Thr Ile Gly Thr Arg Ile His Asn Met Leu Asp Tyr Glu
470             475             480             485 gat gac gac tac aga cca gga ata aag cta aag gca gta gca att gac     1664
Asp Asp Asp Tyr Arg Pro Gly Ile Lys Leu Lys Ala Val Ala Ile Asp
            490             495             500 aga cac gat aac aat cac att ggg gaa gca att att aac att aac ctt     1712
Arg His Asp Asn Asn His Ile Gly Glu Ala Ile Ile Asn Ile Asn Leu
                505             510             515 atc aat tgg aat gat gag cta cct ata ttc gac gag gac gcc tac aac     1760
Ile Asn Trp Asn Asp Glu Leu Pro Ile Phe Asp Glu Asp Ala Tyr Asn
            520             525             530 gtg aca ttt gag gag acg gtc ggt gat ggc ttc cac att ggt aaa tac     1808
Val Thr Phe Glu Glu Thr Val Gly Asp Gly Phe His Ile Gly Lys Tyr
535             540             545
```

| | |
|---|---|
| cgg gct aaa gac aga gac atc ggt gac ata gtc gag cac tcg ata ttg<br>Arg Ala Lys Asp Arg Asp Ile Gly Asp Ile Val Glu His Ser Ile Leu<br>550                555                560              565 | 1856 |
| ggc aac gct gca aac ttc ctg aga att gac ata gat act gga gat gtg<br>Gly Asn Ala Ala Asn Phe Leu Arg Ile Asp Ile Asp Thr Gly Asp Val<br>                570                575              580 | 1904 |
| tac gtg tca cgg gac gat tac ttt gat tat caa aga cag aac gaa atc<br>Tyr Val Ser Arg Asp Asp Tyr Phe Asp Tyr Gln Arg Gln Asn Glu Ile<br>585                590                595 | 1952 |
| ata gtt cag att ctg gct gtt gat aca cta ggt tta cct cag aac agg<br>Ile Val Gln Ile Leu Ala Val Asp Thr Leu Gly Leu Pro Gln Asn Arg<br>                600                605              610 | 2000 |
| gct acc aca cag ctc acg ata ttt ttg gaa gac atc aac aac acg cca<br>Ala Thr Thr Gln Leu Thr Ile Phe Leu Glu Asp Ile Asn Asn Thr Pro<br>615                620                625 | 2048 |
| cct ata ctg cga ctg cca cgt tcc agt cca agt gta gaa gag aac gtt<br>Pro Ile Leu Arg Leu Pro Arg Ser Ser Pro Ser Val Glu Glu Asn Val<br>630                635                640              645 | 2096 |
| gaa gtc ggg cac ccg att acc gag ggg cta acg gcg aca gac cca gac<br>Glu Val Gly His Pro Ile Thr Glu Gly Leu Thr Ala Thr Asp Pro Asp<br>                650                655              660 | 2144 |
| acc aca gcc gat tta cac ttc gag atc gat tgg gac aat tct tac gct<br>Thr Thr Ala Asp Leu His Phe Glu Ile Asp Trp Asp Asn Ser Tyr Ala<br>                665                670              675 | 2192 |
| acg aag cag ggc acc aat gga ccc aac act gca gac tac cac gga tgc<br>Thr Lys Gln Gly Thr Asn Gly Pro Asn Thr Ala Asp Tyr His Gly Cys<br>                680                685              690 | 2240 |
| gta gaa atc ctg acg gta tac cca gat cct gac aat cac ggg aga gct<br>Val Glu Ile Leu Thr Val Tyr Pro Asp Pro Asp Asn His Gly Arg Ala<br>695                700                705 | 2288 |
| gag ggt cac ttg gtg gca cgt gag gtc agt gat ggc gtg acc atc gat<br>Glu Gly His Leu Val Ala Arg Glu Val Ser Asp Gly Val Thr Ile Asp<br>710                715                720              725 | 2336 |
| tac gag aag ttt gag gtg ctg tac ctc gtc gtc agg gtg ata gat cgc<br>Tyr Glu Lys Phe Glu Val Leu Tyr Leu Val Val Arg Val Ile Asp Arg<br>                730                735              740 | 2384 |
| aac act gtc att ggc cct gat tat gac gaa gca atg ctg acg gtg acg<br>Asn Thr Val Ile Gly Pro Asp Tyr Asp Glu Ala Met Leu Thr Val Thr<br>                745                750              755 | 2432 |
| ata atc gat atg aac gac aac tgg ccg ata tgg gcc gac aac acg ctg<br>Ile Ile Asp Met Asn Asp Asn Trp Pro Ile Trp Ala Asp Asn Thr Leu<br>                760                765              770 | 2480 |
| cag cag aca ctg cgc gtg cgc gag atg gcc gac gaa gga gtc atc gtc<br>Gln Gln Thr Leu Arg Val Arg Glu Met Ala Asp Glu Gly Val Ile Val<br>775                780                785 | 2528 |
| ggt aca ctg ctc gcc acc gac ttg gat ggc cct ctc tac aac cga gtc<br>Gly Thr Leu Leu Ala Thr Asp Leu Asp Gly Pro Leu Tyr Asn Arg Val<br>790                795                800              805 | 2576 |
| cgc tac acc atg gtc ccc atc aag gac act cct gat gac cta ata gcg<br>Arg Tyr Thr Met Val Pro Ile Lys Asp Thr Pro Asp Asp Leu Ile Ala<br>                810                815              820 | 2624 |
| atc aac tac gtc acc ggt cag ctg act gtg aac aag ggg caa gca att<br>Ile Asn Tyr Val Thr Gly Gln Leu Thr Val Asn Lys Gly Gln Ala Ile<br>                825                830              835 | 2672 |
| gac gca gat gat cca cct cgc ttc tac ctg tat tac aag gtc act gcc<br>Asp Ala Asp Asp Pro Pro Arg Phe Tyr Leu Tyr Tyr Lys Val Thr Ala<br>                840                845              850 | 2720 |
| agc gat aag tgc tct ctt gac gag ttc ttc cct gtg tgc cca cct gac<br>Ser Asp Lys Cys Ser Leu Asp Glu Phe Phe Pro Val Cys Pro Pro Asp<br>855                860                865 | 2768 |

-continued

| | | |
|---|---|---|
| ccc act tac tgg aat acc gag gga gag ata gcg atc gcg ata acc gat<br>Pro Thr Tyr Trp Asn Thr Glu Gly Glu Ile Ala Ile Ala Ile Thr Asp<br>870                           875                      880                         885 | 2816 |
| acg aac aac aaa att cca cgc gcg gaa aca gat atg ttc cct agt gaa<br>Thr Asn Asn Lys Ile Pro Arg Ala Glu Thr Asp Met Phe Pro Ser Glu<br>                      890                      895                        900 | 2864 |
| aag cgc atc tat gag aac aca ccc aat ggt acc aag atc acg acg atc<br>Lys Arg Ile Tyr Glu Asn Thr Pro Asn Gly Thr Lys Ile Thr Thr Ile<br>            905                      910                        915 | 2912 |
| atc gct agt gac cag gac aga gat cga cca aat aac gcg ctg acg tac<br>Ile Ala Ser Asp Gln Asp Arg Asp Arg Pro Asn Asn Ala Leu Thr Tyr<br>        920                      925                      930 | 2960 |
| aga atc aac tac gca ttc aac cac agg ctg gag aac ttc ttc gca gtg<br>Arg Ile Asn Tyr Ala Phe Asn His Arg Leu Glu Asn Phe Phe Ala Val<br>935                           940                      945 | 3008 |
| gac cct gat act ggt gaa ctg ttt gtc cac ttc acc act agc gaa gtg<br>Asp Pro Asp Thr Gly Glu Leu Phe Val His Phe Thr Thr Ser Glu Val<br>950                           955                      960                      965 | 3056 |
| ttg gac aga gac gga gag gaa ccg gag cat agg atc atc ttc acc atc<br>Leu Asp Arg Asp Gly Glu Glu Pro Glu His Arg Ile Ile Phe Thr Ile<br>            970                      975                        980 | 3104 |
| gtc gat aac ttg gaa ggc gct gga gat ggc aat cag aac aca atc tcc<br>Val Asp Asn Leu Glu Gly Ala Gly Asp Gly Asn Gln Asn Thr Ile Ser<br>        985                      990                      995 | 3152 |
| acg gag gtg cgt gtt ata ctg ctt gat ata aac gac aat aag ccg gaa<br>Thr Glu Val Arg Val Ile Leu Leu Asp Ile Asn Asp Asn Lys Pro Glu<br>1000                        1005                      1010 | 3200 |
| cta cca att cct gat ggc gaa ttt tgg acc gtt tcc gaa ggt gaa gtg<br>Leu Pro Ile Pro Asp Gly Glu Phe Trp Thr Val Ser Glu Gly Glu Val<br>        1015                      1020                      1025 | 3248 |
| gag gga aaa cgc att cca cca gag att cac gca cac gac aga gat gaa<br>Glu Gly Lys Arg Ile Pro Pro Glu Ile His Ala His Asp Arg Asp Glu<br>1030                        1035                      1040                      1045 | 3296 |
| cca ttc aac gac aac tct cgc gtg gga tat gaa att cga tcg atc aaa<br>Pro Phe Asn Asp Asn Ser Arg Val Gly Tyr Glu Ile Arg Ser Ile Lys<br>            1050                      1055                      1060 | 3344 |
| ttg atc aat aga gac atc gag ctt cct caa gat cca ttc aaa ata ata<br>Leu Ile Asn Arg Asp Ile Glu Leu Pro Gln Asp Pro Phe Lys Ile Ile<br>        1065                      1070                      1075 | 3392 |
| acg att gat gat ctc gat acc tgg aaa ttc gtt gga gag ttg gag act<br>Thr Ile Asp Asp Leu Asp Thr Trp Lys Phe Val Gly Glu Leu Glu Thr<br>            1080                      1085                      1090 | 3440 |
| acc atg gac ctt aga gga tac tgg gga acc tat gat gtc gag ata cgt<br>Thr Met Asp Leu Arg Gly Tyr Trp Gly Thr Tyr Asp Val Glu Ile Arg<br>        1095                      1100                      1105 | 3488 |
| gcg ttt gac cac ggt ttc ccg atg ctg gat tca ttc gag acc tac caa<br>Ala Phe Asp His Gly Phe Pro Met Leu Asp Ser Phe Glu Thr Tyr Gln<br>1110                        1115                      1120                      1125 | 3536 |
| cta acc gtc agg cca tac aac ttc cat tca ccg gtg ttt gtg ttc cca<br>Leu Thr Val Arg Pro Tyr Asn Phe His Ser Pro Val Phe Val Phe Pro<br>            1130                      1135                      1140 | 3584 |
| act cct ggc tca acc atc agg ctt tct agg gag cgt gct ata gtc aat<br>Thr Pro Gly Ser Thr Ile Arg Leu Ser Arg Glu Arg Ala Ile Val Asn<br>        1145                      1150                      1155 | 3632 |
| ggt atg ctg gct ctg gct aat atc gcg agc gga gag ttc ctc gac aga<br>Gly Met Leu Ala Leu Ala Asn Ile Ala Ser Gly Glu Phe Leu Asp Arg<br>        1160                      1165                      1170 | 3680 |
| ctc tct gcc act gat gaa gat ggg cta cac gca ggc aga gta act ttc<br>Leu Ser Ala Thr Asp Glu Asp Gly Leu His Ala Gly Arg Val Thr Phe | 3728 |

-continued

```
         1175                1180                1185
tcc ata gct gga aac gat gaa gct gcg gaa tat ttc aat gtg ttg aac      3776
Ser Ile Ala Gly Asn Asp Glu Ala Ala Glu Tyr Phe Asn Val Leu Asn
1190                1195                1200            1205 gac ggt gac aac tca gca atg ctc acg ctg aag caa gca ttg ccc gct      3824
Asp Gly Asp Asn Ser Ala Met Leu Thr Leu Lys Gln Ala Leu Pro Ala
            1210                1215                1220 ggc gtc cag cag ttt gag ttg gtt att cgg gcc acg gac ggg acg          3872
Gly Val Gln Gln Phe Glu Leu Val Ile Arg Ala Thr Asp Gly Gly Thr
        1225                1230                1235 gag ccg gga cct agg agt acc gac tgc tcc gtc act gtg gtg ttt gtg      3920
Glu Pro Gly Pro Arg Ser Thr Asp Cys Ser Val Thr Val Val Phe Val
    1240                1245                1250 atg acg cag gga gac ccc gtg ttc gac gac aac gca gct tct gtc cgc      3968
Met Thr Gln Gly Asp Pro Val Phe Asp Asp Asn Ala Ala Ser Val Arg
1255                1260                1265 ttc gtt gaa aag gaa gct ggt atg tcg gaa aag ttt cag ctg cct cag      4016
Phe Val Glu Lys Glu Ala Gly Met Ser Glu Lys Phe Gln Leu Pro Gln
1270                1275                1280                1285 gcc gat gac ccc aaa aac tac agg tgt atg gac gac tgc cat acc atc      4064
Ala Asp Asp Pro Lys Asn Tyr Arg Cys Met Asp Asp Cys His Thr Ile
            1290                1295                1300 tac tac tct atc gtt gat ggc aac gat ggt gac cac ttc gcc gtg gag      4112
Tyr Tyr Ser Ile Val Asp Gly Asn Asp Gly Asp His Phe Ala Val Glu
        1305                1310                1315 ccg gag act aac gtg atc tat ttg ctg aag ccg ctg gac cgc agc caa      4160
Pro Glu Thr Asn Val Ile Tyr Leu Leu Lys Pro Leu Asp Arg Ser Gln
    1320                1325                1330 cag gag cag tac agg gtc gtg gtg gcg gct tcc aac acg cct ggc ggc      4208
Gln Glu Gln Tyr Arg Val Val Val Ala Ala Ser Asn Thr Pro Gly Gly
1335                1340                1345 acc tcc acc ttg tcc tcc tca ctc ctc acc gtc acc atc ggc gtt cga      4256
Thr Ser Thr Leu Ser Ser Ser Leu Leu Thr Val Thr Ile Gly Val Arg
1350                1355                1360                1365 gaa gca aac cct aga ccg atc ttc gaa agt gaa ttt tac aca gct ggc      4304
Glu Ala Asn Pro Arg Pro Ile Phe Glu Ser Glu Phe Tyr Thr Ala Gly
            1370                1375                1380 gtc tta cac acc gat agc ata cac aag gag ctc gtt tac ctg gcg gca      4352
Val Leu His Thr Asp Ser Ile His Lys Glu Leu Val Tyr Leu Ala Ala
        1385                1390                1395 aaa cat tca gaa ggg ctt cct atc gtc tac tcg ata gat caa gaa acc      4400
Lys His Ser Glu Gly Leu Pro Ile Val Tyr Ser Ile Asp Gln Glu Thr
    1400                1405                1410 atg aaa ata gac gag tcg ttg caa aca gtt gtg gag gac gcc ttc gac      4448
Met Lys Ile Asp Glu Ser Leu Gln Thr Val Val Glu Asp Ala Phe Asp
1415                1420                1425 att aac tct gca acc gga gtc ata tcg ctg aac ttc cag cca aca tct      4496
Ile Asn Ser Ala Thr Gly Val Ile Ser Leu Asn Phe Gln Pro Thr Ser
1430                1435                1440                1445 gtc atg cac ggc agt ttc gac ttc gag gtg gtg gct agt gac acg cgt      4544
Val Met His Gly Ser Phe Asp Phe Glu Val Val Ala Ser Asp Thr Arg
            1450                1455                1460 gga gcg agt gat cga gca aaa gtg tca att tac atg ata tcg act cgc      4592
Gly Ala Ser Asp Arg Ala Lys Val Ser Ile Tyr Met Ile Ser Thr Arg
        1465                1470                1475 gtt aga gta gcc ttc ctg ttc tac aac acg gaa gct gaa gtt aac gag      4640
Val Arg Val Ala Phe Leu Phe Tyr Asn Thr Glu Ala Glu Val Asn Glu
    1480                1485                1490 aga aga aat ttc att gca caa acg ttc gcc aac gcg ttt ggt atg aca      4688
```

-continued

```
                Arg Arg Asn Phe Ile Ala Gln Thr Phe Ala Asn Ala Phe Gly Met Thr
                    1495                1500                1505 tgt aac ata gac agc gtg ctg ccg gct acc gac gcc aac ggc gtg att           4736
Cys Asn Ile Asp Ser Val Leu Pro Ala Thr Asp Ala Asn Gly Val Ile
1510                1515                1520                1525 cgc gag ggg tac aca gaa ctc cag gct cac ttc ata cga gac gac cag           4784
Arg Glu Gly Tyr Thr Glu Leu Gln Ala His Phe Ile Arg Asp Asp Gln
                1530                1535                1540 ccg gtg cca gcc gac tat att gag gga tta ttt acg gaa ctc aat aca           4832
Pro Val Pro Ala Asp Tyr Ile Glu Gly Leu Phe Thr Glu Leu Asn Thr
            1545                1550                1555 ttg cgt gac atc aga gag gta ctg agt act cag caa ttg acg cta ctg           4880
Leu Arg Asp Ile Arg Glu Val Leu Ser Thr Gln Gln Leu Thr Leu Leu
        1560                1565                1570 gac ttt gcg gcg gga ggg tcg gca gtg ctg ccc ggc gga gag tac gcg           4928
Asp Phe Ala Ala Gly Gly Ser Ala Val Leu Pro Gly Gly Glu Tyr Ala
    1575                1580                1585 cta gcg gtg tac atc ctc gcc ggc atc gca gcg tta ctc gcc gtc atc           4976
Leu Ala Val Tyr Ile Leu Ala Gly Ile Ala Ala Leu Leu Ala Val Ile
1590                1595                1600                1605 tgt ctc gct ctc ctc atc gct ttc ttc att agg aac cga aca ctg aac           5024
Cys Leu Ala Leu Leu Ile Ala Phe Phe Ile Arg Asn Arg Thr Leu Asn
                1610                1615                1620 cgg cgc atc gaa gcc ctc aca atc aaa gat gtt cct acg gac atc gag           5072
Arg Arg Ile Glu Ala Leu Thr Ile Lys Asp Val Pro Thr Asp Ile Glu
            1625                1630                1635 cca aac cac gcg tca gta gca gtg cta aac att aac aag cac aca gaa           5120
Pro Asn His Ala Ser Val Ala Val Leu Asn Ile Asn Lys His Thr Glu
        1640                1645                1650 cct ggt tcc aat ccc ttc tat aac ccg gat gtt aag aca cct aac ttc           5168
Pro Gly Ser Asn Pro Phe Tyr Asn Pro Asp Val Lys Thr Pro Asn Phe
    1655                1660                1665 gac act ata agc gaa gta tcc gat gac ctg ctt gat gtc gaa gac ttg           5216
Asp Thr Ile Ser Glu Val Ser Asp Asp Leu Leu Asp Val Glu Asp Leu
1670                1675                1680                1685 gaa cag ttt gga aag gat tac ttc cca ccc gaa aac gaa att gag agc           5264
Glu Gln Phe Gly Lys Asp Tyr Phe Pro Pro Glu Asn Glu Ile Glu Ser
                1690                1695                1700 ctg aat ttt gca cgt aac ccc ata gcg aca cac ggg aac aac ttt ggc           5312
Leu Asn Phe Ala Arg Asn Pro Ile Ala Thr His Gly Asn Asn Phe Gly
            1705                1710                1715 gta aac tca agc ccc tcc aac cca gag ttc tcc aac tcc cag ttt aga           5360
Val Asn Ser Ser Pro Ser Asn Pro Glu Phe Ser Asn Ser Gln Phe Arg
        1720                1725                1730 agt taaactaaat acactttat cacttgcata gacttatgta tttaataatt                 5413
Ser ttcatttttt tacattaaat ataaatgttt tatatgtaat aatagtgtga taaaatgtac         5473
gtaacaatca acatagctgt tgtaggttcg taaataacac actcgtaatg tataagtgtt         5533
atgtttatat atagaaataa aaatattaaa tattaaaaaa aaaaaaaaaa aaaaaaaa           5592

<210> SEQ ID NO 6
<211> LENGTH: 1734
<212> TYPE: PRT
<213> ORGANISM: Spodoptera frugiperda

<400> SEQUENCE: 6

Met Ala Val Asp Val Arg Ile Leu Thr Ala Thr Leu Leu Val Leu Thr
1               5                   10                  15
```

-continued

```
Thr Ala Thr Ala Gln Arg Asp Arg Cys Gly Tyr Met Val Glu Ile Pro
             20                  25                  30

Arg Pro Asp Arg Pro Asp Phe Pro Pro Gln Asn Phe Asp Gly Leu Thr
         35                  40                  45

Trp Ala Gln Gln Pro Leu Leu Pro Ala Glu Asp Arg Glu Glu Val Cys
 50                  55                  60

Leu Asn Asp Tyr Glu Pro Asp Pro Trp Ser Asn Asn His Gly Asp Gln
 65                  70                  75                  80

Arg Ile Tyr Met Glu Glu Ile Glu Gly Pro Val Val Ile Ala Lys
                 85                  90                  95

Ile Asn Tyr Gln Gly Asn Thr Pro Pro Gln Ile Arg Leu Pro Phe Arg
                100                 105                 110

Val Gly Ala Ala His Met Leu Gly Ala Glu Ile Arg Glu Tyr Pro Asp
            115                 120                 125

Ala Thr Gly Asp Trp Tyr Leu Val Ile Thr Gln Arg Gln Asp Tyr Glu
130                 135                 140

Thr Pro Asp Met Gln Arg Tyr Thr Phe Asp Val Ser Val Glu Gly Gln
145                 150                 155                 160

Ser Leu Val Val Thr Val Arg Leu Asp Ile Val Asn Ile Asp Asp Asn
                165                 170                 175

Ala Pro Ile Ile Glu Met Leu Glu Pro Cys Asn Leu Pro Glu Leu Val
            180                 185                 190

Glu Pro His Val Thr Glu Cys Lys Tyr Ile Val Ser Asp Ala Asp Gly
        195                 200                 205

Leu Ile Ser Thr Ser Val Met Ser Tyr His Ile Asp Ser Glu Arg Gly
210                 215                 220

Asp Glu Lys Val Phe Glu Leu Ile Arg Lys Asp Tyr Pro Gly Asp Trp
225                 230                 235                 240

Thr Lys Val Tyr Met Val Leu Glu Leu Lys Lys Ser Leu Asp Tyr Glu
                245                 250                 255

Glu Asn Pro Leu His Ile Phe Arg Val Thr Ala Ser Asp Ser Leu Pro
            260                 265                 270

Asn Asn Arg Thr Val Val Met Met Val Glu Val Glu Asn Val Glu His
        275                 280                 285

Arg Asn Pro Arg Trp Met Glu Ile Phe Ala Val Gln Gln Phe Asp Glu
290                 295                 300

Lys Gln Ala Lys Ser Phe Thr Val Arg Ala Ile Asp Gly Asp Thr Gly
305                 310                 315                 320

Ile Asn Lys Pro Ile Phe Tyr Arg Ile Glu Thr Glu Asp Glu Asp Lys
                325                 330                 335

Glu Phe Phe Ser Ile Glu Asn Ile Gly Glu Gly Arg Asp Gly Ala Arg
            340                 345                 350

Phe His Val Ala Pro Ile Asp Arg Asp Tyr Leu Lys Arg Asp Met Phe
        355                 360                 365

His Ile Arg Ile Ile Ala Tyr Lys Gln Gly Asp Asn Asp Lys Glu Gly
370                 375                 380

Glu Ser Ser Phe Glu Thr Ser Ala Asn Val Thr Ile Ile Asn Asp
385                 390                 395                 400

Ile Asn Asp Gln Arg Pro Glu Pro Phe His Lys Glu Tyr Thr Ile Ser
                405                 410                 415

Ile Met Glu Glu Thr Ala Met Thr Leu Asp Leu Gln Glu Phe Gly Phe
            420                 425                 430

His Asp Arg Asp Ile Gly Pro His Ala Gln Tyr Asp Val His Leu Glu
```

-continued

```
            435                 440                 445
Ser Ile Gln Pro Glu Gly Ala His Thr Ala Phe Tyr Ile Ala Pro Glu
    450                 455                 460

Glu Gly Tyr Gln Ala Gln Ser Phe Thr Ile Gly Thr Arg Ile His Asn
465                 470                 475                 480

Met Leu Asp Tyr Glu Asp Asp Tyr Arg Pro Gly Ile Lys Leu Lys
                485                 490                 495

Ala Val Ala Ile Asp Arg His Asp Asn Asn His Ile Gly Glu Ala Ile
                500                 505                 510

Ile Asn Ile Asn Leu Ile Asn Trp Asn Asp Glu Leu Pro Ile Phe Asp
            515                 520                 525

Glu Asp Ala Tyr Asn Val Thr Phe Glu Glu Thr Val Gly Asp Gly Phe
        530                 535                 540

His Ile Gly Lys Tyr Arg Ala Lys Asp Arg Asp Ile Gly Asp Ile Val
545                 550                 555                 560

Glu His Ser Ile Leu Gly Asn Ala Ala Asn Phe Leu Arg Ile Asp Ile
                565                 570                 575

Asp Thr Gly Asp Val Tyr Val Ser Arg Asp Asp Tyr Phe Asp Tyr Gln
            580                 585                 590

Arg Gln Asn Glu Ile Ile Val Gln Ile Leu Ala Val Asp Thr Leu Gly
        595                 600                 605

Leu Pro Gln Asn Arg Ala Thr Thr Gln Leu Thr Ile Phe Leu Glu Asp
    610                 615                 620

Ile Asn Asn Thr Pro Pro Ile Leu Arg Leu Pro Arg Ser Ser Pro Ser
625                 630                 635                 640

Val Glu Glu Asn Val Glu Val Gly His Pro Ile Thr Glu Gly Leu Thr
                645                 650                 655

Ala Thr Asp Pro Asp Thr Thr Ala Asp Leu His Phe Glu Ile Asp Trp
            660                 665                 670

Asp Asn Ser Tyr Ala Thr Lys Gln Gly Thr Asn Gly Pro Asn Thr Ala
        675                 680                 685

Asp Tyr His Gly Cys Val Glu Ile Leu Thr Val Tyr Pro Asp Pro Asp
    690                 695                 700

Asn His Gly Arg Ala Glu Gly His Leu Val Ala Arg Glu Val Ser Asp
705                 710                 715                 720

Gly Val Thr Ile Asp Tyr Glu Lys Phe Glu Val Leu Tyr Leu Val Val
                725                 730                 735

Arg Val Ile Asp Arg Asn Thr Val Ile Gly Pro Asp Tyr Asp Glu Ala
            740                 745                 750

Met Leu Thr Val Thr Ile Ile Asp Met Asn Asp Asn Trp Pro Ile Trp
        755                 760                 765

Ala Asp Asn Thr Leu Gln Gln Thr Leu Arg Val Arg Glu Met Ala Asp
    770                 775                 780

Glu Gly Val Ile Val Gly Thr Leu Leu Ala Thr Asp Leu Asp Gly Pro
785                 790                 795                 800

Leu Tyr Asn Arg Val Arg Tyr Thr Met Val Pro Ile Lys Asp Thr Pro
                805                 810                 815

Asp Asp Leu Ile Ala Ile Asn Tyr Val Thr Gly Gln Leu Thr Val Asn
            820                 825                 830

Lys Gly Gln Ala Ile Asp Ala Asp Pro Pro Arg Phe Tyr Leu Tyr
        835                 840                 845

Tyr Lys Val Thr Ala Ser Asp Lys Cys Ser Leu Asp Glu Phe Phe Pro
    850                 855                 860
```

```
Val Cys Pro Pro Asp Pro Thr Tyr Trp Asn Thr Glu Gly Glu Ile Ala
865                 870                 875                 880

Ile Ala Ile Thr Asp Thr Asn Asn Lys Ile Pro Arg Ala Glu Thr Asp
            885                 890                 895

Met Phe Pro Ser Glu Lys Arg Ile Tyr Glu Asn Thr Pro Asn Gly Thr
        900                 905                 910

Lys Ile Thr Thr Ile Ile Ala Ser Asp Gln Asp Arg Asp Arg Pro Asn
            915                 920                 925

Asn Ala Leu Thr Tyr Arg Ile Asn Tyr Ala Phe Asn His Arg Leu Glu
        930                 935                 940

Asn Phe Phe Ala Val Asp Pro Asp Thr Gly Glu Leu Phe Val His Phe
945                 950                 955                 960

Thr Thr Ser Glu Val Leu Asp Arg Asp Gly Glu Pro Glu His Arg
            965                 970                 975

Ile Ile Phe Thr Ile Val Asp Asn Leu Glu Gly Ala Gly Asp Gly Asn
        980                 985                 990

Gln Asn Thr Ile Ser Thr Glu Val Arg Val Ile Leu Leu Asp Ile Asn
        995                 1000                1005

Asp Asn Lys Pro Glu Leu Pro Ile Pro Asp Gly Glu Phe Trp Thr Val
        1010                1015                1020

Ser Glu Gly Glu Val Gly Lys Arg Ile Pro Pro Glu Ile His Ala
1025                1030                1035                1040

His Asp Arg Asp Glu Pro Phe Asn Asp Asn Ser Arg Val Gly Tyr Glu
            1045                1050                1055

Ile Arg Ser Ile Lys Leu Ile Asn Arg Asp Ile Glu Leu Pro Gln Asp
            1060                1065                1070

Pro Phe Lys Ile Ile Thr Ile Asp Asp Leu Asp Thr Trp Lys Phe Val
            1075                1080                1085

Gly Glu Leu Glu Thr Thr Met Asp Leu Arg Gly Tyr Trp Gly Thr Tyr
            1090                1095                1100

Asp Val Glu Ile Arg Ala Phe Asp His Gly Phe Pro Met Leu Asp Ser
1105                1110                1115                1120

Phe Glu Thr Tyr Gln Leu Thr Val Arg Pro Tyr Asn Phe His Ser Pro
            1125                1130                1135

Val Phe Val Phe Pro Thr Pro Gly Ser Thr Ile Arg Leu Ser Arg Glu
            1140                1145                1150

Arg Ala Ile Val Asn Gly Met Leu Ala Leu Ala Asn Ile Ala Ser Gly
            1155                1160                1165

Glu Phe Leu Asp Arg Leu Ser Ala Thr Asp Gly Asp Gly Leu His Ala
            1170                1175                1180

Gly Arg Val Thr Phe Ser Ile Ala Gly Asn Asp Glu Ala Ala Glu Tyr
1185                1190                1195                1200

Phe Asn Val Leu Asn Asp Gly Asp Asn Ser Ala Met Leu Thr Leu Lys
            1205                1210                1215

Gln Ala Leu Pro Ala Gly Val Gln Gln Phe Glu Leu Val Ile Arg Ala
            1220                1225                1230

Thr Asp Gly Gly Thr Glu Pro Gly Pro Arg Ser Thr Asp Cys Ser Val
            1235                1240                1245

Thr Val Val Phe Val Met Thr Gln Gly Asp Pro Val Phe Asp Asp Asn
            1250                1255                1260

Ala Ala Ser Val Arg Phe Val Glu Lys Glu Ala Gly Met Ser Glu Lys
1265                1270                1275                1280
```

-continued

Phe Gln Leu Pro Gln Ala Asp Pro Lys Asn Tyr Arg Cys Met Asp
            1285                1290                1295

Asp Cys His Thr Ile Tyr Tyr Ser Ile Val Asp Gly Asn Asp Gly Asp
                1300                1305                1310

His Phe Ala Val Glu Pro Glu Thr Asn Val Ile Tyr Leu Leu Lys Pro
            1315                1320                1325

Leu Asp Arg Ser Gln Gln Glu Gln Tyr Arg Val Val Ala Ala Ser
            1330                1335                1340

Asn Thr Pro Gly Gly Thr Ser Thr Leu Ser Ser Ser Leu Leu Thr Val
1345                1350                1355                1360

Thr Ile Gly Val Arg Glu Ala Asn Pro Arg Pro Ile Phe Glu Ser Glu
            1365                1370                1375

Phe Tyr Thr Ala Gly Val Leu His Thr Asp Ser Ile His Lys Glu Leu
            1380                1385                1390

Val Tyr Leu Ala Ala Lys His Ser Glu Gly Leu Pro Ile Val Tyr Ser
            1395                1400                1405

Ile Asp Gln Glu Thr Met Lys Ile Asp Glu Ser Leu Gln Thr Val Val
            1410                1415                1420

Glu Asp Ala Phe Asp Ile Asn Ser Ala Thr Gly Val Ile Ser Leu Asn
1425                1430                1435                1440

Phe Gln Pro Thr Ser Val Met His Gly Ser Phe Asp Phe Glu Val Val
            1445                1450                1455

Ala Ser Asp Thr Arg Gly Ala Ser Asp Arg Ala Lys Val Ser Ile Tyr
            1460                1465                1470

Met Ile Ser Thr Arg Val Arg Val Ala Phe Leu Phe Tyr Asn Thr Glu
            1475                1480                1485

Ala Glu Val Asn Glu Arg Arg Asn Phe Ile Ala Gln Thr Phe Ala Asn
            1490                1495                1500

Ala Phe Gly Met Thr Cys Asn Ile Asp Ser Val Leu Pro Ala Thr Asp
1505                1510                1515                1520

Ala Asn Gly Val Ile Arg Glu Gly Tyr Thr Glu Leu Gln Ala His Phe
            1525                1530                1535

Ile Arg Asp Asp Gln Pro Val Pro Ala Asp Tyr Ile Glu Gly Leu Phe
            1540                1545                1550

Thr Glu Leu Asn Thr Leu Arg Asp Ile Arg Glu Val Leu Ser Thr Gln
            1555                1560                1565

Gln Leu Thr Leu Leu Asp Phe Ala Ala Gly Gly Ser Ala Val Leu Pro
            1570                1575                1580

Gly Gly Glu Tyr Ala Leu Ala Val Tyr Ile Leu Ala Gly Ile Ala Ala
1585                1590                1595                1600

Leu Leu Ala Val Ile Cys Leu Ala Leu Leu Ile Ala Phe Phe Ile Arg
            1605                1610                1615

Asn Arg Thr Leu Asn Arg Arg Ile Glu Ala Leu Thr Ile Lys Asp Val
            1620                1625                1630

Pro Thr Asp Ile Glu Pro Asn His Ala Ser Val Ala Val Leu Asn Ile
            1635                1640                1645

Asn Lys His Thr Glu Pro Gly Ser Asn Pro Phe Tyr Asn Pro Asp Val
            1650                1655                1660

Lys Thr Pro Asn Phe Asp Thr Ile Ser Glu Val Ser Asp Asp Leu Leu
1665                1670                1675                1680

Asp Val Glu Asp Leu Glu Gln Phe Gly Lys Asp Tyr Phe Pro Pro Glu
            1685                1690                1695

Asn Glu Ile Glu Ser Leu Asn Phe Ala Arg Asn Pro Ile Ala Thr His

```
                1700              1705              1710
Gly Asn Asn Phe Gly Val Asn Ser Ser Pro Ser Asn Pro Glu Phe Ser
        1715              1720              1725

Asn Ser Gln Phe Arg Ser
    1730

<210> SEQ ID NO 7
<211> LENGTH: 1604
<212> TYPE: DNA
<213> ORGANISM: Ostrinia nubilalis

<400> SEQUENCE: 7
tccgaattct tcttcaacct catcgacaac ttcttttctg acggtgacgg taggagaaac      60
caggacgaag ttgaaatatt tgtcgttcta ttggatgtga acgacaacgc tcctgagatg     120
ccatcgcctg atgaactccg gtttgatgtt tccgaaggag cagttgctgg tgtccgtgta     180
ctcccagaaa tctacgcacc tgacagggat gaaccagaca cggacaactc gcgtgtcggt     240
tacggaatcc tggacctcac gatcaccgac cgagacatcg aggtgccgga tctcttcacc     300
atgatctcga ttgaaaacaa aactgggaa cttgagaccg ctatggactt gaggggtat      360 tggggcactt acgaaatatt cattgaggcc ttcgaccacg gctacccgca gcagaggtcc     420
aacgggacgt acacactggt cattcgcccc tacaacttcc accacctgt gttcgtgttc      480 ccgcaacccg actccgtcat cggctctct agggagcgcg caacagaagg cggggtcctg      540
gcgacggctg ccaacgagtt cctggagccg atctacgcca ccgacgagga cggcctccac     600
gcgggcagcg tcacgttcca cgtccaggga atgaggagg ccgttcagta ctttgatata      660
actgaagtgg gagcaggaga aaatagcggg cagcttatat tacgccagct tttcccagag     720
caaatcagac aattcaggat cacgatccgg gccacagacg gcggcacgga gcccggcccg     780 cttttggaccg acgtcacgtt ttcggtggtc ttcgtaccca gcagggcga cccagtgttc     840 agcgaaaatg cagctactgt tgccttcttc gagggtgaag aaggcctcca tgagagtttt     900
gagctgccgc aagcagaaga ccttaaaaac cacctctgcg aagatgactg ccaagatatc     960
tactacaggt ttattgacgg caacaacgag ggtctgttcg tgctggacca gtcgagcaac    1020
gtcatctccc ttgcgcagga gttggaccgc gaggttgcca cgtcttacac gctgcacatc    1080
gcggcgagca actcgcccga cgccactggg atccctctgc agacttccat cctcgttgtc    1140
acggtcaatg taagagaagc gaacccgcgc ccaattttcg agcaggacct ttacacagcg    1200
ggcatttcga cgttggacag cattggccgg gaattgctta ccgtcagggc gagccacaca    1260
gaagacgaca ccatcacgta catcatagac cgtgcgagca tgcagctgga cagcagccta    1320
gaagccgtgc gcgactcggc cttcacgctg catgcgacca ccggcgtgct ttcgctcaat    1380
atgcagccca ccgcttccat gcacggcatg ttcgagttcg acgtcatcgc tacggataca    1440
gcatctgcaa tcgacacagc tcgtgtgaaa gtctacctca tctcatcgca aaaccgcgtg    1500
tccttcattt tcgataacca acttgagacc gttgagcaga acagaaattt catagcggcc    1560
acgttcagca ccgggttcaa catgacgtgt aacatcgacc aagt                     1604

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
```

```
gttamygtga gagaggcaga ycc                                              23

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
ggatrttaag mgtcagyacw ccg                                              23

<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 10
tccgaattct tcttyaacct catcgayaac tt                                    32

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 11
cgcaagctta cttggtcgat gttrcasgtc at                                    32
```

BT TOXIN RECEPTORS FROM LEPIDOPTERAN INSECTS

CROSS-REFERENCE TO RELATED APPLICATION

This application is a divisional application of U.S. application Ser. No. 09/715,909, filed Nov. 17, 2000, now U.S. Pat. No. 7,060,491, which claims the benefit of U.S. Provisional Application Ser. No. 60/234,099, filed Sep. 21, 2000 and U.S. Provisional Application Ser. No. 60/166,285, filed Nov. 18, 1999, the contents of which are herein incorporated by reference in their entirety.

FIELD OF THE INVENTION

The field of the invention is manipulating Bt toxin susceptibility in plant pests. The field of the invention relates to the isolation and characterization of nucleic acid and polypeptides for a novel Bt toxin receptor. The nucleic acid and polypeptides are useful in developing new insecticides.

BACKGROUND OF THE INVENTION

Traditionally, growers used chemical pesticides as a means to control agronomically important pests. The introduction of transgenic plants carrying the delta-endotoxin from *Bacillus thuringiensis* (Bt) afforded a non-chemical method of control. Bt toxins have traditionally been categorized by their specific toxicity towards specific insect categories. For example, the CryI group of toxins are toxic to Lepidoptera. The CryI group includes, but is not limited to, CryIA(a), CryIA(b) and CryIA(c). See Hofte et al (1989) *Microbiol Rev* 53: 242-255.

Lepidopteran insects cause considerable damage to maize crops throughout North America and the world. One of the leading pests is *Ostrinia nubilalis*, commonly called the European Corn Borer (ECB). Genes encoding the crystal proteins CryIA(b) and CryIA(c) from Bt have been introduced into maize as a means of ECB control. These transgenic maize hybrids have been effective in control of ECB. However, developed resistance to Bt toxins presents a challenge in pest control. See McGaughey et al. (1998) *Nature Biotechnology* 16: 144-146; Estruch et al. (1997) *Nature Biotechnology* 15:137-141; Roush et al. (1997) *Nature Biotechnology* 15 816-817; and Hofte et al (1989) *Microbiol Rev* 53: 242-255.

The primary site of action of CryI toxins is in the brush border membranes of the midgut epithelia of susceptible insect larvae such as lepidopteran insects. CryIA toxin binding polypeptides have been characterized from a variety of Lepidopteran species. A CryIA(c) binding polypeptide with homology to an aminopeptidase N has been reported from *Manduca sexta, Lymantria dispar, Helicoverpa zea* and *Heliothis virescens*. See Knight et al (1994) *Mol Micro* 11: 429-436; Lee et al. (1996) *Appl Environ Micro* 63: 2845-2849; Gill et al. (1995) *J. Biol. Chem* 270: 27277-27282; and Garczynski et al. (1991) *Appl Environ Microbiol* 10: 2816-2820.

Another Bt toxin binding polypeptide (BTR1) cloned from *M. sexta* has homology to the cadherin polypeptide superfamily and binds CryIA(a), CryIA(b) and CryIA(c). See Vadlamudi et al. (1995) *J Biol Chem* 270(10):5490-4, Keeton et al. (1998) *Appl Environ Microbiol* 64(6):2158-2165; Keeton et al. (1997) *Appl Environ Microbiol* 63(9):3419-3425 and U.S. Pat. No. 5,693,491.

A subsequently cloned homologue to BTR1 demonstrated binding to CryIA(a) from *Bombyx mori* as described in Ihara et al. (1998) *Comparative Biochemistry and Physiology, Part B* 120:197-204 and Nagamatsu et al. (1998) *Biosci. Biotechnol. Biochem.* 62(4):727-734.

Identification of the plant pest binding polypeptides for Bt toxins are useful for investigating Bt toxin-Bt toxin receptor interactions, selecting and designing improved toxins, developing novel insecticides, and new Bt toxin resistance management strategies.

SUMMARY OF THE INVENTION

Compositions and methods for modulating susceptibility of a cell to Bt toxins are provided. The compositions include Bt toxin receptor polypeptides, and fragments and variants thereof, from the lepidopteran insects European corn borer (ECB, *Ostrinia nubilalis*), corn earworm (CEW, *Heliothis Zea*), and fall armyworm (FAW, *Spodoptera frugiperda*). The polypeptides bind CryIA toxins, more particularly CryIA(b). Nucleic acids encoding the polypeptides, antibodies specific to the polypeptides, as well as nucleic acid constructs for expressing the polypeptides in cells of interest are also provided.

The methods are useful for investigating the structure-function relationships of Bt toxin receptors; investigating the toxin-receptor interactions; elucidating the mode of action of Bt toxins; screening and identifying novel Bt toxin receptor ligands including novel insecticidal toxins; and designing and developing novel Bt toxin receptor ligands.

The methods are useful for managing Bt toxin resistance in plant pests, and protecting plants against damage by plant pests.

BRIEF DESCRIPTION OF THE DRAWINGS

FIG. 1 schematically depicts the location of the signal sequence, putative glycosilation sites, cadherin-like domains, transmembrane segment, CryIA binding region and protein kinase C phosphorylation site of the Bt toxin receptor from *Ostrinia nubilalis*; the nucleotide sequence of the receptor set forth in SEQ ID NO: 1 and the corresponding deduced amino acid sequence in SEQ ID NO:2.

DETAILED DESCRIPTION OF THE INVENTION

The invention is directed to novel receptor polypeptides that bind Bt toxin, the receptor being derived from the order *lepidoptera*. The receptors of the invention include those receptor polypeptides that bind Bt toxin and are derived from the lepidopteran superfamily Pyraloidea and particularly from the species *Ostrinia*, specifically *Ostrinia nubilalis*; those derived from *Spodoptera frugiperda* (*S. frugperda*); and those derived from *Heliothus Zea* (*H. Zea*). The polypeptides have homology to members of the cadherin superfamily of proteins. Accordingly, compositions of the invention include isolated polypeptides that are involved in Bt toxin binding. In particular, the present invention provides for isolated nucleic acid molecules comprising nucleotide sequences encoding the amino acid sequences shown in SEQ ID NOs: 2, 4, and 6; or the nucleotide sequences having the DNA sequences deposited in a plasmid in a bacterial host as Patent Deposit No. PTA-278, PTA-1760, and PTA-2222. Further provided are polypeptides having an amino acid sequence encoded by a nucleic acid molecule described herein, for example those set forth in SEQ ID NOs: 1, 3, and 5; those deposited in a plasmid in a bacterial host as Patent Deposit Nos. PTA-278, PTA-1760, and PTA-2222; and fragments and variants thereof.

Plasmids containing the nucleotide sequences of the invention were deposited with the Patent Depository of the American Type Culture Collection (ATCC), Manassas, Va. on Jun. 25, 1999; Apr. 25, 2000; and Jul. 11, 2000; and assigned Patent Deposit Nos. PTA-278, PTA-1760, and PTA-2222. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The term "nucleic acid" refers to all forms of DNA such as cDNA or genomic DNA and RNA such as mRNA, as well as analogs of the DNA or RNA generated using nucleotide analogs. The nucleic acid molecules can be single stranded or double stranded. Strands can include the coding or non-coding strand.

The invention encompasses isolated or substantially purified nucleic acid or polypeptide compositions. An "isolated" or "purified" nucleic acid molecule or polypeptide, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably polypeptide encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A polypeptide that is substantially free of cellular material includes preparations of polypeptide having less than about 30%, 20%, 10%, 5%, (by dry weight) of contaminating polypeptide. When the polypeptide of the invention or biologically active portion thereof is recombinantly produced, preferably culture medium represents less than about 30%, 20%, 10%, or 5% (by dry weight) of chemical precursors or non-polypeptide-of-interest chemicals.

It is understood, however, that there are embodiments in which preparations that do not contain the substantially pure polypeptide may also be useful. Thus, less pure preparations can be useful where the contaminating material does not interfere with the specific desired use of the peptide. The compositions of the invention also encompass fragments and variants of the disclosed nucleotide sequences and the polypeptides encoded thereby.

The compositions of the invention are useful for, among other uses, expressing the receptor polypeptides in cells of interest to produce cellular or isolated preparations of the polpeptides for investigating the structure-function relationships of Bt toxin receptors; investigating the toxin-receptor interactions; elucidating the mode of action of Bt toxins; screening and identifying novel Bt toxin receptor ligands including novel insecticidal toxins; and designing and developing novel Bt toxin receptor ligands including novel insecticidal toxins.

The isolated nucleotide sequences encoding the receptor polypeptides of the invention are expressed in a cell of interest; and the Bt toxin receptor polypeptides produced by the expression is utilized in intact cell or in-vitro receptor binding assays, and/or intact cell toxicity assays. Methods and conditions for Bt toxin binding and toxicity assays are known in the art and include but are not limited to those described in U.S. Pat. No. 5,693,491; T. P. Keeton et al. (1998) *Appl.* *Environ. Microbiol.* 64(6):2158-2165; B. R. Francis et al. (1997) *Insect Biochem. Mol. Biol.* 27(6):541-550; T. P. Keeton et al. (1997) *Appl. Environ. Microbiol.* 63(9):3419-3425; R. K. Vadlamudi et al. (1995) *J. Biol. Chem.* 270(10):5490-5494; Ihara et al. (1998) *Comparative Biochem. Physiol. B* 120:197-204; Nagamatsu et al. (1998) *Biosci. Biotechnol. Biochem.* 62(4):727-734, herein incorporated by reference. Such methods could be modified by one of ordinary skill in the art to develop assays utilizing the polypeptides of the invention.

By "cell of interest" is intended any cell in which expression of the polypeptides of the invention is desired. Cells of interest include, but are not limited to mammalian, avian, insect, plant, bacteria, fungi and yeast cells. Cells of interest include but are not limited to cultured cell lines, primary cell cultures, cells in vivo, and cells of transgenic organisms.

The methods of the invention encompass using the polypeptides encoded by the nucleotide sequences of the invention in receptor binding and/or toxicity assays to screen candidate ligands and identify novel Bt toxin receptor ligands, including receptor agonists and antagonists. Candidate ligands include molecules available from diverse libraries of small molecules created by combinatorial synthetic methods. Candidate ligands also include, but are not limited to antibodies, peptides, and other small molecules designed or deduced to interact with the receptor polypeptides of the invention. Candidate ligands include but are not limited to peptide fragments of the receptor, anti-receptor antibodies, antiidiotypic antibodies mimicking one or more receptor binding domains of a toxin, fusion proteins produced by combining two or more toxins or fragments thereof, and the like. Ligands identified by the screening methods of the invention include potential novel insecticidal toxins, the insecticidal activity of which can be determined by known methods; for example, as described in U.S. Pat. No. 5,407,454; U.S. application Ser. No. 09/218,942; U.S. application Ser. No. 09/003,217.

The invention provides methods for screening for ligands that bind to the polypeptides described herein. Both the polypeptides and relevant fragments thereof (for example, the toxin binding domain) can be used to screen by assay for compounds that bind to the receptor and exhibit desired binding characteristics. Desired binding characteristics include, but are not limited to binding affinity, binding site specificity, association and dissociation rates, and the like. The screening assays could be intact cell or in vitro assays which include exposing a ligand binding domain to a sample ligand and detecting the formation of a ligand-binding polypeptide complex. The assays could be direct ligand-receptor binding assays or ligand competition assays.

In one embodiment, the methods comprise providing at least one Bt toxin receptor polypeptide of the invention, contacting the polypeptide with a sample and a control ligand under conditions promoting binding; and determining binding characteristics of sample ligands, relative to control ligands. The methods encompass any method known to the skilled artisan which can be used to provide the polypeptides of the invention in a binding assay. For in vitro binding assays, the polypeptide may be provided as isolated, lysed, or homogenized cellular preparations. Isolated polypeptides may be provided in solution, or immobilized to a matrix. Methods for immobilizing polypeptides are well known in the art, and include but are not limited to construction and use of fusion polypeptides with commercially available high affinity ligands. For example, GST fusion proteins can be adsorbed onto glutathione sepharose beads (Sigma Chemical, St. Louis, Mo.) or glutathione derivatized microtitre plates. The polypeptides can also be immobilized utilizing well techniques in the art utilizing conjugation of biotin and streptavidin. The polypeptides can also be immobilized utilizing well known techniques in the art utilizing chemical conjugation (linking) of polypeptides to a matrix. Alternatively, the polypeptides may be provided in intact cell binding assays in which the polypeptides are generally expressed as cell surface Bt toxin receptors.

The invention provides methods utilizing intact cell toxicity assays to screen for ligands that bind to the receptor polypeptides described herein and confer toxicity upon a cell of interest expressing the polypeptide. A ligand selected by this screening is a potential insecticidal toxin to insects expressing the receptor polypeptides, particularly enterally. This deduction is premised on theories that insect specificity of a particular Bt toxin is determined by the presence of the receptor in specific insect species, or that binding of the toxins is specific for the receptor of some insect species and is bind is insignificant or nonspecific for other variant receptors. See, for example Hofte et al (1989) *Microbiol Rev* 53: 242-255. The toxicity assays include exposing, in intact cells expressing a polypeptide of the invention, the toxin binding domain of the polypeptide to a sample ligand and detecting the toxicity effected in the cell expressing the polypeptide. By "toxicity" is intended the decreased viability of a cell. By "viability" is intended the ability of a cell to proliferate and/or differentiate and/or maintain its biological characteristics in a manner characteristic of that cell in the absence of a particular cytotoxic agent.

In one embodiment, the methods of the present invention comprise providing at least one cell surface Bt toxin receptor polypeptide of the invention comprising an extracellular toxin binding domain, contacting the polypeptide with a sample and a control ligand under conditions promoting binding, and determining the viability of the cell expressing the cell surface Bt toxin receptor polypeptide, relative to the control ligand.

By "contacting" is intended that the sample and control agents are presented to the intended ligand binding site of the polypeptides of the invention.

By "conditions promoting binding" is intended any combination of physical and biochemical conditions that enables a ligand of the polypeptides of the invention to determinably bind the intended polypeptide over background levels. Examples of such conditions for binding of CryI toxins to Bt toxin receptors, as well as methods for assessing the binding, are known in the art and include but are not limited to those described in Keeton et al. (1998) *Appl Environ Microbiol* 64(6): 2158-2165; Francis et al. (1997) *Insect Biochem Mol Biol* 27(6):541-550; Keeton et al. (1997) *Appl Environ Microbiol* 63(9):3419-3425; Vadlamudi et al. (1995) *J Biol Chem* 270(10):5490-5494; Ihara et al. (1998) *Comparative Biochemistry and Physiology*, Part B 120:197-204; and Nagamatsu et al. (1998) *Biosci. Biotechnol. Biochem.* 62(4):727-734, the contents of which are herein incorporated by reference. In this aspect of the present invention, known and commercially available methods for studying protein-protein interactions, such as yeast and/or bacterial two-hybrid systems could also be used. Two-hybrid systems are available from, for example, CLONTECH (Palo Alto, Calif.) or Display Systems Biotech Inc. (Vista, Ca).

The compositions and screening methods of the invention are useful for designing and developing novel Bt toxin receptor ligands including novel insecticidal toxins. Various candidate ligands; ligands screened and characterized for binding, toxicity, and species specificity; and/or ligands having known characteristics and specificities, could be linked or modified to produce novel ligands having particularly desired characteristics and specificities. The methods described herein for assessing binding, toxicity and insecticidal activity could be used to screen and characterize the novel ligands.

In one embodiment of the present invention, the sequences encoding the receptors of the invention, and variants and fragments thereof, are used with yeast and bacterial two-hybrid systems to screen for Bt toxins of interest (for example, more specific and/or more potent toxins), or for insect molecules that bind the receptor and can be used in developing novel insecticides.

By "linked" is intended that a covalent bond is produced between two or more molecules. Known methods that can be used for modification and/or linking of polypeptide ligands such as toxins, include but are not limited to mutagenic and recombinogenic approaches including but not limited to site-directed mutagenesis, chimeric polypeptide construction and DNA shuffling. Such methods are described in further detail below. Known polypeptide modification methods also include methods for covalent modification of polypeptides. "Operably linked" means that the linked molecules carry out the function intended by the linkage.

The compositions and screening methods of the present invention are useful for targeting ligands to cells expressing the receptor polypeptides of the invention. For targeting, secondary polypeptides, and/or small molecules which do not bind the receptor polypeptides of the invention are linked with one or more primary ligands which bind the receptor polypeptides; including but not limited to CryI A toxin; more particularly CryI A(b) toxin or a fragment thereof. By this linkage, any polypeptide and/or small molecule linked to a primary ligand could be targeted to the receptor polypeptide, and thereby to a cell expressing the receptor polypeptide; wherein the ligand binding site is available at the extracellular surface of the cell.

In one embodiment of the invention, at least one secondary polypeptide toxin is linked with a primary CryI A toxin capable of binding the receptor polypeptides of the invention to produce a combination toxin which is targeted and toxic to insects expressing the receptor for the primary toxin. Such insects include those of the order *lepidoptera*, superfamily Pyraloidea and particularly from the species *Ostrinia*, specifically *Ostrinia nubilalis*. Such insects include the lepidopterans *S. frugiperda* and *H. Zea*. Such a combination toxin is particularly useful for eradicating or reducing crop damage by insects which have developed resistance to the primary toxin.

For expression of the Bt toxin receptor polypeptides of the invention in a cell of interest, the Bt toxin receptor sequences are provided in expression cassettes. The cassette will include 5' and 3' regulatory sequences operably linked to a Bt toxin receptor sequence of the invention. In this aspect of the present invention, by "operably linked" is intended a functional linkage between a promoter and a second sequence, wherein the promoter sequence initiates and mediates transcription of the DNA sequence corresponding to the second sequence. In reference to nucleic acids, generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the Bt toxin receptor sequence to be under the transcriptional regulation of the regulatory regions. The expression cassette may additionally contain selectable marker genes.

The expression cassette will include in the 5'-3' direction of transcription, a transcriptional and translational initiation region, a Bt toxin receptor nucleotide sequence of the invention, and a transcriptional and translational termination region functional in host cells. The transcriptional initiation region, the promoter, may be native or analogous, or foreign or heterologous to the plant host. Additionally, the promoter may be the natural sequence or alternatively a synthetic sequence. By "foreign" is intended that the transcriptional initiation region is not found in the native host cells into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of Bt toxin receptor in the cell of interest. Thus, the phenotype of the cell is altered.

The termination region may be native with the transcriptional initiation region, may be native with the operably linked DNA sequence of interest, or may be derived from another source.

Where appropriate, the gene(s) may be optimized for increased expression in a particular transformed cell of interest. That is, the genes can be synthesized using host cell-preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding polypeptide (BiP), (Macejak et al. (1991) *Nature* 353:90-94); untranslated leader from the coat polypeptide mRNA of alfalfa mosaic virus (AMV RNA 4) (Jobling et al. (1987) *Nature* 325:622-625); tobacco mosaic virus leader (TMV) (Gallie et al. (1989) in *Molecular Biology of mRNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Using the nucleic acids of the present invention, the polypeptides of the invention could be expressed in any cell of interest, the particular choice of the cell depending on factors such as the level of expression and/or receptor activity desired. Cells of interest include, but are not limited to conveniently available mammalian, plant, insect, bacteria, and yeast host cells. The choice of promoter, terminator, and other expression vector components will also depend on the cell chosen. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda-derived P L promoter and N-gene ribosome binding site (Shimatake et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235; Mosbach et al. (1983) *Nature* 302: 543-545).

A variety of eukaryotic expression systems such as yeast, insect cell lines, plant and mammalian cells, are known to those of skill in the art. The sequences of the present invention can be expressed in these eukaryotic systems. In some embodiments, transformed/transfected plant cells are employed as expression systems for production of the proteins of the instant invention.

Synthesis of heterologous proteins in yeast is well known. Sherman, F. et al. (1982) *Methods in Yeast Genetics*, Cold Spring Harbor Laboratory is a well recognized work describing the various methods available to produce the protein in yeast. Two widely utilized yeast for production of eukaryotic proteins are *Saccharomyces cerevisia* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay or other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the COS, HEK293, BHK21, and CHO cell lines. Expression vectors for these cells can include expression control sequences, such as an origin of replication, a promoter (e.g., the CMV promoter, a HSV tk promoter orpgk (phosphoglycerate kinase promoter)), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992). A particular example of mammalian cells for expression of a Bt toxin receptor and assessing Bt toxin cytotoxicity mediated by the receptor, includes embryonic 293 cells. See U.S. Pat. No. 5,693,491, herein incorporated by reference.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See Schneider et al. (1987) *J Embryol. Exp. Morphol.* 27: 353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773-781). Additionally, gene sequences to control replication in the host cell may be incorporated into the vector such as those found in bovine papilloma virus-type vectors. Saveria-Campo, M., Bovine Papilloma Virus DNA a Eukaryotic Cloning Vector in *DNA Cloning Vol. II a Practical Approach*, D. M. Glover, ed., IRL Pres, Arlington, Va. pp. 213-238 (1985).

In a particular embodiment of the invention, it may be desirable to negatively control receptor binding; particularly, when toxicity to a cell is no longer desired or if it is desired to reduce toxicity to a lower level. In this case, ligand-receptor polypeptide binding assays can be used to screen for compounds which bind to the receptor but do not confer toxicity to a cell expressing the receptor. The examples of a molecule that can be used to block ligand binding include an antibody that specifically recognizes the ligand binding domain of the receptor such that ligand binding is decreased or prevented as desired.

In another embodiment, receptor polypeptide expression could be blocked by the use of antisense molecules directed against receptor RNA or ribozymes specifically targeted to this receptor RNA. It is recognized that with the provided nucleotide sequences, antisense constructions, complementary to at least a portion of the messenger RNA (mRNA) for the Bt toxin receptor sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

Fragments and variants of the disclosed nucleotide sequences and polypeptides encoded thereby are encompassed by the present invention. By "fragment" is intended a portion of the nucleotide sequence, or a portion of the amino acid sequence, and hence a portion of the polypeptide encoded thereby. Fragments of a nucleotide sequence may encode polypeptide fragments that retain the biological activity of the native polypeptide and, for example, bind Bt toxins. Alternatively, fragments of a nucleotide sequence that are useful as hybridization probes generally do not encode fragment polypeptides retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a Bt toxin receptor nucleotide sequence that encodes a biologically active portion of a Bt toxin receptor polypeptide of the invention will encode at least 15, 25, 30, 50, 100, 150, 200 or 250 contiguous amino acids, or up to the total number of amino acids present in a full-length Bt toxin receptor polypeptide of the invention (for example, 1717, 1730, and 1734 amino acids for SEQ ID NOs:2, 4, and 6, respectively. Fragments of a Bt toxin receptor nucleotide sequence that are useful as hybridization probes for PCR primers generally need not encode a biologically active portion of a Bt toxin receptor polypeptide.

Thus, a fragment of a Bt toxin receptor nucleotide sequence may encode a biologically active portion of a Bt toxin receptor polypeptide, or it may be a fragment that can be used as a hybridization probe or PCR primer using methods disclosed below. A biologically active portion of a Bt toxin receptor polypeptide can be prepared by isolating a portion of one of the Bt toxin receptor nucleotide sequences of the invention, expressing the encoded portion of the Bt toxin receptor polypeptide (e.g., by recombinant expression in vitro), and assessing the activity of the encoded portion of the Bt toxin receptor polypeptide. Nucleic acid molecules that are fragments of a Bt toxin receptor nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length Bt toxin receptor nucleotide sequence disclosed herein (for example, 5498, 5527, and 5614 nucleotides for SEQ ID NOs: 1, 3, and 5, respectively).

By "variants" is intended substantially similar sequences. For nucleotide sequences, conservative variants include those sequences that, because of the degeneracy of the genetic code, encode the amino acid sequence of one of the Bt toxin receptor polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis, but which still encode a Bt toxin receptor protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, activity as described herein (for example, Bt toxin binding activity). Such variants may result from, for example, genetic polymorphism or from human manipulation. Biologically active variants of a native Bt toxin receptor protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The polypeptides of the invention may be altered in various ways including amino acid substitutions, deletions, truncations, and insertions. Methods for such manipulations are generally known in the art. For example, amino acid sequence variants of the Bt toxin receptor polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired toxin binding activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. For example, it is recognized that at least about 10, 20, 50, 100, 150, 200, 250, 300, 350, 400, 450, 500, 550, 600, 650, 700, 750, 800, 850, 900, 950, and up to 960 amino acids may be deleted from the N-terminus of a polypeptide that has the amino acid sequence set forth in SEQ ID NO:2, and still retain binding function. It is further recognized that at least about 10, 20, 30, 40, 50, 60, 70, 80, 90, 100, 110, and up to 119 amino acids may be deleted from the C-terminus of a polypeptide that has the amino acid sequence set forth in SEQ ID NO:2, and still retain binding function. Deletion variants of the invention that encompass polypeptides having these deletions. It is recognized that deletion variants of the invention that retain binding function encompass polypeptides having these N-terminal or C-terminal deletions, or having any deletion combination thereof at both the C- and the N-termini.

However, when it is difficult to predict the exact effect of the substitution, deletion, or insertion in advance of doing so, one skilled in the art will appreciate that the effect will be evaluated by routine screening assays. That is, the activity can be evaluated by receptor binding and/or toxicity assays. See, for example, U.S. Pat. No. 5,693,491; T. P. Keeton et al. (1998) *Appl. Environ. Microbiol.* 64(6):2158-2165; B. R. Francis et al. (1997) *Insect Biochem. Mol. Biol.* 27(6):541-550; T. P. Keeton et al. (1997) *Appl. Environ. Microbiol* 63(9): 3419-3425; R. K. Vadlamudi et al. (1995) *J. Biol. Chem.* 270(10):5490-5494; Ihara et al. (1998) *Comparative Biochem. Physiol. B* 120:197-204; Nagamatsu et al. (1998) *Biosci. Biotechnol. Biochem.* 62(4):727-734, herein incorporated by reference.

Variant nucleotide sequences and polypeptides also encompass sequences and polypeptides derived from a mutagenic and recombinogenic procedure such as DNA shuffling. With such a procedure, one or more different toxin receptor coding sequences can be manipulated to create a new toxin receptor, including but not limited to a new Bt toxin receptor, possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Bt toxin receptor gene of the invention and other known Bt toxin receptor genes to obtain a new gene coding for a polypeptide with an improved property of interest, such as an increased ligand affinity in the case of a receptor. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,448.

Where the receptor polypeptides of the invention are expressed in a cell and associated with the cell membrane (for example, by a transmembrane segment), in order for the receptor of the invention to bind a desired ligand, for example a CryI A toxin, the receptor's ligand binding domain must be available to the ligand. In this aspect, it is recognized that the native Bt toxin receptor of the invention is oriented such that the toxin binding site is available extracellularly.

Accordingly, in methods comprising use of intact cells, the invention provides cell surface Bt-toxin receptors. By a "cell surface Bt toxin receptor" is intended a membrane-bound receptor polypeptide comprising at least one extracellular Bt toxin binding site. A cell surface receptor of the invention comprises an appropriate combination of signal sequences and transmembrane segments for guiding and retaining the receptor at the cell membrane such that that toxin binding site is available extracellularly. Where native Bt toxin receptors are used for expression, deduction of the composition and configuration of the signal sequences and transmembrane segments is not necessary to ensure the appropriate topology of the polypeptide for displaying the toxin binding site extracellularly. As an alternative to native signal and transmembrane sequences, heterologous signal and transmembrane sequences could be utilized to produce a cell surface receptor polypeptide of the invention.

It is recognized that it may be of interest to generate Bt toxin receptors that are capable of interacting with the receptor's ligands intracellularly in the cytoplasm, in the nucleus or other organelles, in other subcellular spaces; or in the extracellular space. Accordingly, the invention encompasses variants of the receptors of the invention, wherein one or more of the segments of the receptor polypeptide is modified to target the polypeptide to a desired intra- or extracellular location.

Also encompassed by the invention are receptor fragments and variants that are useful, among other things, as binding antagonists that will compete with a cell surface receptor of the invention. Such a fragment or variant can, for example, bind a toxin but not be able to confer toxicity to a particular cell. In this aspect, the invention provides secreted receptors, more particularly secreted Bt toxin receptors; or receptors that are not membrane bound. The secreted receptors of the invention can contain a heterologous or homologous signal sequence facilitating its secretion from the cell expressing the receptors; and further comprise a secretion variation in the region corresponding to transmembrane segments. By "secretion variation" is intended that amino acids corresponding to a tranmembrne segment of a membrane bound receptor comprise one or more deletions, substitutions, insertions, or any combination thereof; such that the region no longer retains the requisite hydrophobicity to serve as a transmembrane segment. Sequence alterations to create a secretion variation can be tested by confirming secretion of the polypeptide comprising the variation from the cell expressing the polypeptide.

The polypeptides of the invention can be purified from cells that naturally express it, purified from cells that have been altered to express it (i.e. recombinant) or synthesized using polypeptide synthesis techniques that are well known in the art. In one embodiment, the polypeptide is produced by recombinant DNA methods. In such methods a nucleic acid molecule encoding the polypeptide is cloned into an expression vector as described more fully herein and expressed in an appropriate host cell according to known methods in the art. The polypeptide is then isolated from cells using polypeptide purification techniques well known to those of ordinary skill in the art. Alternatively, the polypeptide or fragment can be synthesized using peptide synthesis methods well known to those of ordinary skill in the art.

The invention also encompasses fusion polypeptides in which one or more polypeptides of the invention are fused with at least one polypeptide of interest. In one embodiment, the invention encompasses fusion polypeptides in which a heterologous polypeptide of interest has an amino acid sequence that is not substantially homologous to the polypeptide of the invention. In this embodiment, the polypeptide of the invention and the polypeptide of interest may or may not be operatively linked. An example of operative linkage is fusion in-frame so that a single polypeptide is produced upon translation. Such fusion polypeptides can, for example, facilitate the purification of a recombinant polypeptide.

In another embodiment, the fused polypeptide of interest may contain a heterologous signal sequence at the N-terminus facilitating its secretion from specific host cells. The expression and secretion of the polypeptide can thereby be increased by use of the heterologous signal sequence.

The invention is also directed to polypeptides in which one or more domains in the polypeptide described herein are operatively linked to heterologous domains having homologous functions. Thus, the toxin binding domain can be replaced with a toxin binding domain for other toxins. Thereby, the toxin specificity of the receptor is based on a toxin binding domain other than the domain encoded by Bt toxin receptor but other characteristics of the polypeptide, for example, membrane localization and topology is based on Bt toxin receptor.

Alternatively, the native Bt toxin binding domain may be retained while additional heterologous ligand binding domains, including but not limited to heterologous toxin binding domains are comprised by the receptor. Thus, the invention also encompasses fusion polypeptides in which a polypeptide of interest is a heterologous polypeptide comprising a heterologous toxin binding domains. Examples of heterologous polypeptides comprising CryI toxin binding domains include, but are not limited to Knight et al (1994) *Mol Micro* 11: 429-436; Lee et al. (1996) *Appl Environ Micro* 63: 2845-2849; Gill et al. (1995) *J Biol Chem* 270: 27277-27282; Garczynski et al. (1991) *Appl Environ Microbiol* 10: 2816-2820; Vadlamudi et al. (1995) *J Biol Chem* 270(10): 5490-4, U.S. Pat. No. 5,693,491.

The Bt toxin receptor peptide of the invention may also be fused with other members of the cadherin superfamily. Such fusion polypeptides could provide an important reflection of the binding properties of the members of the superfamily. Such combinations could be further used to extend the range of applicability of these molecules in a wide range of systems or species that might not otherwise be amenable to native or relatively homologous polypeptides. The fusion constructs could be substituted into systems in which a native construct would not be functional because of species specific constraints. Hybrid constructs may further exhibit desirable or unusual characteristics otherwise unavailable with the combinations of native polypeptides.

Polypeptide variants encompassed by the present invention include those that contain mutations that either enhance or decrease one or more domain functions. For example, in the toxin binding domain, a mutation may be introduced that increases or decreases the sensitivity of the domain to a specific toxin.

As an alternative to the introduction of mutations, increase in function may be provided by increasing the copy number of ligand binding domains. Thus, the invention also encompasses receptor polypeptides in which the toxin binding domain is provided in more than one copy.

The invention further encompasses cells containing receptor expression vectors comprising the Bt toxin receptor sequences, and fragments and variants thereof. The expression vector can contain one or more expression cassettes used to transform a cell of interest. Transcription of these genes can be placed under the control of a constitutive or inducible promoter (for example, tissue—or cell cycle-preferred).

Where more than one expression cassette utilized, the cassette that is additional to the cassette comprising at least one receptor sequence of the invention, can comprise either a receptor sequence of the invention or any other desired sequences.

The nucleotide sequences of the invention can be used to isolate homologous sequences in insect species other than *ostrinia*, particularly other lepidopteran species, more particularly other *Pyraloidea* species.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (version 3.0, copyright 1997); and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN and the ALIGN PLUS programs are based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid sequence is immunologically cross reactive with the polypeptide encoded by the second nucleic acid sequence.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention can be used to isolate corresponding sequences from other organisms, particularly other insects, more particularly other lepidopteran species. In this manner, methods such as PCR, hybridization, and the like can be used to identify such sequences based on their sequence homology to the sequences set forth herein. Sequences isolated based on their sequence identity to the entire Bt toxin receptor sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) PCR Strategies (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the Bt toxin receptor sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire Bt toxin receptor sequence disclosed herein, or one or more portions thereof, may be used as a probe capable of specifically hybridizing to corresponding Bt toxin receptor sequences and messenger RNAs. To achieve specific hybridization under a variety of conditions, such probes include sequences that are unique among Bt toxin receptor sequences and are preferably at least about 10 nucleotides in length, and most preferably at least about 20 nucleotides in length. Such probes may be used to amplify corresponding Bt toxin receptor sequences from a chosen plant organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a Bt toxin receptor protein and which hybridize under stringent conditions to the Bt toxin receptor sequences disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity.

The compositions and screening methods of the invention are useful for identifying cells expressing the BT toxin receptors of the invention, and variants and homologues thereof. Such identification could utilize detection methods at the protein level, such as ligand-receptor binding; or at the nucleotide level. Detection of the polypeptide could be in situ by means of in situ hybridization of tissue sections but may also be analyzed by bulk polypeptide purification and subsequent analysis by Western blot or immunological assay of a bulk preparation. Alternatively, receptor gene expression can be detected at the nucleic acid level by techniques well known to those of ordinary skill in any art using complimentary polynucleotides to assess the levels of genomic DNA, mRNA, and the like. As an example, PCR primers complimentary to the nucleic acid of interest can be used to identify the level of expression. Tissues and cells identified as expressing the receptor sequences of the invention are determined to be susceptible to toxins which bind the receptor polypeptides.

Where the source of the cells identified to express the receptor polypeptides of the invention is an organism, for example an insect plant pest, the organism is determined to be susceptible to toxins capable of binding the polypeptides. In a particular embodiment, identification is in a lepidopteran plant pesr expressing the Bt toxin receptor of the invention.

The invention encompasses antibody preparations with specificity against the polypeptides of the invention. In further embodiments of the invention, the antibodies are used to detect receptor expression in a cell.

In one aspect, the invention is particularly drawn to compositions and methods for modulating susceptibility of plant pests to Bt toxins. However, it is recognized that the methods and compositions could be used for modulating susceptibility of any cell or organism to the toxins. By "modulating" is intended that the susceptibility of a cell or organism to the cytotoxic effects of the toxin is increased or decreased. By "suceptibility" is intended that the viability of a cell contacted with the toxin is decreased. Thus the invention encompasses expressing the cell surface receptor polypeptides of the invention to increase susceptibility of a target cell or organ to Bt toxins. Such increases in toxin susceptibility are useful for medical and veterinary purposes in which eradication or reduction of viability of a group of cells is desired. Such increases in susceptibility are also useful for agricultural applications in which eradication or reduction of population of particular plant pests is desired.

Plant pests of interest include, but are not limited to insects, nematodes, and the like. Nematodes include parasitic nematodes such as root-knot, cyst, lesion, and renniform nematodes, etc.

The following examples are offered by way of illustration and not by way of limitation.

EXPERIMENTAL

Example 1

Isolation of EC Bt Toxin Receptor

Standard recombinant methods well known to those of ordinary skill in the art were carried out. For library construction, total RNA was isolated from the midgut of European corn borer (ECB), *Ostrinia nubilalis*. Corn borer larvae (for example, a mix of stage 2, 3, and 4, equal weight) can be pulverized in liquid nitrogen, homogenized, and total RNA extracted by standard procedures. PolyA RNA can be isolated from the total RNA with standard PolyA isolation procedures, such as the PolyATact system from Promega Corporation, Madison, Wis. cDNA synthesis can then be performed and, for example, unidirectional cDNA libraries can be constructed according to known and commercial procedures, such as the ZAP Express cDNA synthesis kit from Stratagene, La Jolla, Calif. cDNA can be amplified by PCR, sized and properly digested with restriction fragments to be ligated into a vector. Subcloned cDNA can be sequenced to identify sequences with the proper peptide to identity corresponding to published sequences. These fragments can be used to probe genomic or cDNA libraries corresponding to a specific host, such as *Ostrinia nubilalis*, to obtain a full length coding sequence. Probes can also be made based on Applicants disclosed sequences. The coding sequence can then be ligated into a desired expression cassette and used to transform a host cell according to standard transformation procedures. Such an expression cassette can be part of a commercially available vector and expression system; for example, the pET system from Novagen Inc. (Madison, Wis.). Additional vectors that can be used for expression include pBKCMV, pBKRSV, pPbac and pMbac (Stratagene Inc.), pFASTBacl (Gibco BRL) and other common bacterial, baculovirus, mammalian, and yeast expression vectors.

All vectors were constructed using standard molecular biology techniques as described for example in Sambrook et al., (1989) *Molecular Cloning: A Laboratory Manual* (2$^{nd}$ ed., Cold Spring Harbor Laboratory: Cold Spring Harbor, N.Y.).

Expression is tested by ligand blotting and testing for Bt toxin binding. Ligand blotting, binding, and toxicity are tested by known methods; for example, as described in Martinez-Ramirez (1994) *Biochem. Biophys. Res. Comm.* 201: 782-787; Vadlarnudi et al. (1995) *J Biol Chem* 270(10):5490-4, Keeton et al. (1998) *Appl Environ Microbiol* 64(6):2158-2165; Keeton et al. (1997) *Appl Environ Microbiol* 63(9): 3419-3425; Ihara et al. (1998) *Comparative Biochemistry and Physiology*, Part B 120:197-204; Nagamatsu et al. (1998) *Biosci. Biotechnol. Biochem.* 62(4):718-726 and Nagamatsu et al. (1998) *Biosci. Biotechnol. Biochem.* 62(4):727-734.

Identifying the CryIA(b) binding polypeptide in ECB was done by ligand blotting brush border membrane vesicle polypeptides and probing those polypeptides for binding with CryIA(b) toxin. Two polypeptides, approximately 210 and 205 kDa, were found to bind to CryIA(b). Blotting and binding were done essentially as described in the preceding paragraph.

Degenerate primers for RT-PCR were designed based on known CryI toxin binding polypeptide sequences from *Manducca sexta* and *Bombyx mori*. The primers are shown below. cDNA was constructed from total midgut RNA (cDNA synthesis kit GibcoBrL). Degenerate primers were used to amplify products of the expected size. The annealing temperature used was 53° C. in generation of the 280 bp fragment and 55° C. when generating the 1.6 kb fragment.

A 280 bp fragment was obtained from ECB midgut RNA. Upon cloning and sequencing, the fragment was identified as having homology with the Bt toxin receptor 1 polypeptide (BTR1) described in Vadlamudi et al. (1995) *J Biol Chem* 270(10):5490-4.

A similar approach was used to generate a 1.6 kilobase pair clone. The sequence of primers used to generate the 280 base pair fragment were:

```
Primer BTRD1S:
5'GTTAMYGTGAGAGAGGCAGAYCC3',      (SEQ ID NO:8)
and

Primer BTRD5A:
5'GGATRTTAAGMGTCAGYACWCCG3'.      (SEQ ID NO:9)
```

The sequence of primers used to generate the 1.6 kb fragment were:

```
Primer BTRD6S:                          (SEQ ID NO:10)
5'TCCGAATTCTTCTTYAACCTCATCGAYAACTT3',
and Primer BTRD7A:                          (SEQ ID NO:11)
5'CGCAAGCTTACTTGGTCGATGTTRCASGTCAT3'
```

The 1.6 kb fragment clone was ligated in an E. coli expression vector, pET-28a-c(+), and expressed using the pET system (Novagen Inc., Madison, Wis.). Purified polypeptide encoded by this 1.6 kb fragment demonstrated binding to CryIA(b) in ligand blots. An ECB midgut cDNA library was generated and screened using this 1.6 kb clone, generating 120 positive plaques. Thirty of these plaques were chosen for secondary screening and fifteen of those plaques were purified and sent for DNA sequencing.

The obtained nucleotide sequence of the selected Bt toxin receptor clone from ECB is set forth in SEQ ID NO: 1. The total length of the clone is 5498 base pairs. The coding sequences are residues 162-5312. The CryIA binding site is encoded by residues 4038-4547. The predicted transmembrane domain is encoded by residues 4872-4928. The corresponding deduced amino acid sequence for this Bt toxin receptor clone from ECB is set forth in SEQ ID NO: 2.

The purified polypeptide generated from the 1.6 kb fragment set forth in SEQ ID NO:7 was used to inoculate rabbits for the production of polyclonal antibodies. On zoo western blots prepared from brush border membrane vesicles from various insect species, this set of antibodies specifically recognized ECB Bt toxin receptor polypeptides, in comparison to Bt toxin receptor homologues polypeptides from other insect species. Rabbit polyclonal antibodies were also raised from a purified polypeptide corresponding to amino acids 1293-1462 of SEQ ID NO:2.

Example 2

Isolation of CEW and FAW Bt Toxin Receptor Orthologues cDNA encoding a full-length Bt toxin receptor from corn earworm (CEW, *Heliothis Zea*) was isolated. The nucleotide sequence for this cDNA is set forth in SEQ ID NO: 3. Nucleotides 171-5360 correspond to the open reading frame. Nucleotides 4917-4973 correspond to the transmembrane region. Nucleotides 4083-4589 correspond to the CryIA binding site. The deduced corresponding amino acid sequence for the CEW Bt toxin receptor is set forth in SEQ ID NO: 4.

cDNA encoding a full-length Bt toxin receptor from fall armyworm (FAW, *Spodoptera frugiperda*) was isolated. The nucleotide sequence for this cDNA is set forth in SEQ ID NO: 5. Nucleotides 162-5363 correspond to the open reading frame. Nucleotides 4110-4616 correspond to the CryIA binding site. Nucleotides 4941-4997 correspond to the transmembrane region. Nucleotides 162-227 correspond to a signal peptide. The deduced corresponding amino acid sequence for the FAW Bt toxin receptor is set forth in SEQ ID NO: 6.

Example 3

Binding and Cell Death in Lepidopteran Insect Cells Expressing the Bt Toxin Receptors of the Invention An in vitro system is developed to demonstrate the functionality of a Bt toxin receptor of the invention. The results disclosed in this example demonstrate that the ECB Bt toxin receptor of the invention (SEQ ID NOs:1 and 2) is specifically involved in the binding and killing action of CryIAb toxin.

Well known molecular biological methods are used in cloning and expressing the ECB Bt toxin receptor in Sf9 cells. A baculovirus expression system (Gibco BRL Catalogue No. 10359-016) is used according to the manufacturer's provided protocols and as described below. *S. frugiperda* (Sf9) cells obtained from ATCC (ATCC-CRL 1711) are grown at 27° C. in Sf-900 II serum free medium (Gibco BRL, Catalogue No. 10902-088). These cells, which are not susceptible to CryIAb toxin, are transfected with an expression construct (pFastBacl bacmid, Gibco BRL catalogue NO. 10360-014) comprising an operably linked Bt toxin receptor of the invention (SEQ ID NO: 1) downstream of a polyhedrin promoter. Transfected Sf9 cells express the ECB Bt toxin receptor and are lysed in the presence of CryIAb toxin. Toxin specificities, binding parameters, such as Kd values, and half maximal doses for cellular death and/or toxicity are also determined.

For generating expression constructs, the ECB Bt toxin receptor cDNA (SEQ ID NO:1) is subjected to appropriate restriction digestion, and the resulting cDNA comprising the full-length coding region is ligated into the donor plasmid pFastBac1 multiple cloning site. Following transformation and subsequent transposition, recombinant bacmid DNA comprising the ECB Bt toxin receptor (RBECB1) is isolated. As a control, recombinant bacmid DNA comprising the reporter gene β-glucuronidase (RBGUS) is similarly constructed and isolated.

For transfection, 2 μg each RBECB1 or RBGUS DNA is mixed with 6 μl of CellFectin (GibcoBRL catalogue NO. 10362-010) in 100 μl of Sf900 medium, and incubated at room temperature for 30 minutes. The mixture is then diluted with 0.8 ml Sf-900 medium. Sf9 cells ($10^6$/ml per 35 mm well) are washed once with Sf-900 medium, mixed with the DNA/CellFectin mixture, added to the well, and incubated at room temperature for 5 hours. The medium is removed and 2 ml of Sf-900 medium containing penicillin and streptomycin is added to the well. 3-5 days after transfection, Western blotting is used to examine protein expression.

For Western blotting, 100 μl of cell lysis buffer (50 mM Tris, pH7.8, 150 mM NaCl, 1% Nonidet P-40) is added to the well. The cells are scraped and subjected to 16,000×g centrifugation. Pellet and supernatant are separated and subjected to Western blotting. An antibody preparation against ECB Bt toxin receptor (Example 1) is used as first antibody. Alkaline phosphatase-labelled anti-rabbit IgG is used as secondary antibody. Western blot results indicate that the full length ECB Bt toxin receptor of the invention (SEQ ID NOs:1 and 2) is expressed in the cell membrane of these cells.

For determining GUS activity, the medium of the cells transfected with RBGUS is removed. The cells and the medium are separately mixed with GUS substrate and assayed for the well known enzymatic activity. GUS activity assays indicate that this reporter gene is actively expressed in the transfected cells.

For determining toxin susceptibility, Cry toxins including but not limited to CryIA, CryIB, CryIC, CryID, CryIE, CryIF, CryII, Cry2, Cry3, and Cry9 toxins (Schnepf E. et al. (1998) *Microbiology and Molecular Biology Reviews* 62(3): 775-806) are prepared by methods known in the art. Crystals are dissolved in pH 10.0, 50 mM carbonate buffer and treated with trypsin. Active fragments of Cry proteins are purified by chromatography. Three to five days after transfection, cells are washed with phosphate buffered saline (PBS). Different concentrations of active fragments of Cry toxins are applied to the cells. At different time intervals, the cells are examined under the microscope to readily determine susceptibility to the toxins. Alternatively, cell death, viability and/or toxicity is quantified by methods well known in the art. See, for example, In Situ Cell Death Detection Kits available from Roche Biochemicals (Catalogue Nos. 2 156 792, 1 684 809, and 1 684 817), and LIVE/DEAD® Viability/Cytotoxicity Kit available from Molecular Probes (catalogue No. L-3224).

A dose-dependent response of RBECB1-transfected cells to CryIAb is readily observed, with determined Kd values well within the range for many receptors. Control cells, e.g. those transfected with pFastBac1 bacmid without an insert or those transfected with RBGus are not significantly affected by CryIAb. Interaction with other Cry toxins are similarly characterized.

This in vitro system is not only be used to verify the functionality of putative Bt-toxin receptors, but also used as a tool to determine the active site(s) and other functional domains of the toxin and the receptor. Furthermore, the system is used as a cell-based high throughput screen. For example, methods for distinguishing live versus dead cells by differential dyes are known in the art. This allows for aliquots of transfected cells to be treated with various toxin samples and to serve as a means for screening the toxin samples for desired specificity or binding characteristics. Since the system is used to identify the specificity of Cry protein receptors, it is a useful tool in insect resistance management.

Example 4

Expression of the ECB Bt Toxin Receptor in Toxin Susceptible Stages of the Insect's Life Cycle Total RNA was isolated from the eggs, pupae, adults, and the 1st through the 5th instar developmental stages, using TRIzol Reagent (Gibco BRL) essentially as instructed by the manufacturer.(Gibco BRL). The RNA was quantitated and 20 ug of each sample was loaded onto a formaldehyde agarose gel and electrophoresed at constant voltage. The RNA was then transferred to a nylon membrane via neutral capillary transfer and cross-linked to the membrane using ultraviolet light. For hybridization, a 460 base pair ECB Bt toxin receptor DNA probe (bases 3682 to 4141 in SEQ ID NO:1) was constructed from a 460 base pair fragment prepared according to the manufacturer's protocol for Amersham Rediprime II random prime labeling system. The denatured probe was added to the membrane that had been prehybridized for at least 3 hours at 65° C. and allowed to incubate with gentle agitation for at least 12 hours at 65° C. Following hybridization, the membranes were washed at 65° C. for 1 hour with 1/4×0.5M NaCl, 0.1M NaPO4 (ph 7.0), 6 mM EDTA and 1% SDS solution followed by two 1 hour washes in the above solution without SDS. The membrane was air dried briefly, wrapped in Saran Wrap and exposed to X-ray film.

An ECB Bt toxin receptor transcript of 5.5 kilobase was expressed strongly in the larval instars with much reduced expression in the pupal stage. The expression levels appeared to be fairly consistent from first to fifth instar, while decreasing markedly in the pupal stage. There were no detectable transcripts in either the egg or adult stages. These results indicate that the ECB Bt toxin transcript is being produced in the susceptible stages of the insects life cycle, while not being produced in stages resistant to the toxic effects of CryIAb.

Example 5

Tissue and Subcellular Expression of the ECB Bt Toxin Receptor

Fifth instar ECB were dissected to isolate the following tissues: fat body (FB), malpighian tubules (MT), hind gut (HG), anterior midgut (AM) and posterior midgut (PM). Midguts from fifth instar larvae were also isolated for brush border membrane vesicle (BBMV) preparation using the well known protocol by Wolfersberger et al. (1987) Comp. Biochem. Physiol. 86A:301-308. Tissues were homogenized in Tris buffered saline, 0.1% tween-20, centrifuged to pellet insoluble material, and transferred to a fresh tube. 50 ug of protein from each preparation was added to SDS sample buffer and B-mercaptoethanol, heated to 100° C. for 10 minutes and loaded onto a 4-12% Bis-Tris gel (Novex). After electrophoresis, the proteins were transferred to a nitrocellulose membrane using a semi-dry apparatus. The membrane was blocked in 5% nonfat dry milk buffer for 1 hour at room temperature with gentle agitation. The primary antibody (Example 1) was added to a final dilution of 1:5000 and allowed to hybridize for 1 hour. The blot was then washed three times for 20 minutes each in nonfat milk buffer. The blot was then hybridized with the secondary antibody (goat anti-rabbit with alkaline phosphatase conjugate) at a dilution of 1:10000 for 1 hour at room temperature. Washes were performed as before. The bands were visualized by using the standard chemiluminescent protocol (Tropix western light protein detection kit).

The ECB Bt toxin receptor protein was only visible in the BBMV enriched lane, and not detected in any of the other ECB tissues types. This result indicates that the expression of the ECB Bt toxin receptor protein is at very low levels, since the BBMV preparation is a 20-30 fold enriched fraction of the midgut brush border. The result supports propositions that the ECB Bt toxin receptor is an integral membrane protein uniquely associated with the brush border. It also demonstrates that the ECB Bt toxin receptor is expressed in the envisioned target tissue for CryIAb toxins. However, the result does not necessarily rule out expression in other tissue types, albeit the expression of this protein in those tissues may be lower than in the BBMV enriched fraction.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated *Ostrinia nubialis* insect receptor polypeptide having *Bacillus thuringiensis* (Bt) Cry1A toxin binding activity and an amino acid sequence selected from the group consisting of:
   a) the amino acid sequence set forth in SEQ ID NO:2;
   b) an amino acid sequence having at least 95% sequence identity to the amino acid sequence set forth in SEQ NO:2;
   c) the amino acid sequence encoded by the nucleotide sequence set forth in SEQ ID NO:1; and,
   d) an amino acid sequence encoded by a nucleotide sequence having at least 95% sequence identity to the nucleotide sequence set forth in SEQ ID NO:1.

2. A fusion polypeptide comprising the polypeptide of claim 1, and at least one additional Bt toxin receptor polypeptide.

3. The fusion polypeptide of claim 2, wherein said additional Bt toxin receptor polypeptide has Cry1A toxin binding activity.

* * * * *

UNITED STATES PATENT AND TRADEMARK OFFICE
CERTIFICATE OF CORRECTION

PATENT NO. : 7,572,889 B2  Page 1 of 1
APPLICATION NO. : 11/192967
DATED : August 11, 2009
INVENTOR(S) : Flannagan et al.

It is certified that error appears in the above-identified patent and that said Letters Patent is hereby corrected as shown below:

Column 2,

Line 51, "frugperda" should read --frugiperda--.

Column 7,

Line 44, "picomavirus" should read --picornavirus--;

Line 55, "*mRNA*" should read --*RNA*--.

Column 9,

Line 43, "orpgk" should read --or pgk--.

Column 22,

Line 28, "Vadlarnudi" should read --Vadlamudi--.

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,572,889 B2 | Page 1 of 1 |
| APPLICATION NO. | : 11/192967 | |
| DATED | : August 11, 2009 | |
| INVENTOR(S) | : Flannagan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this

Seventh Day of September, 2010

David J. Kappos
*Director of the United States Patent and Trademark Office*